(12) United States Patent (10) Patent No.: US 9,149,605 B2
Kleinstreuer (45) Date of Patent: Oct. 6, 2015

(54) METHODS AND DEVICES FOR TARGETED INJECTION OF MICROSPHERES

(76) Inventor: Clement Kleinstreuer, Raleigh, NC (US)

(*) Notice: Subject to any disclaimer, the term of this patent is extended or adjusted under 35 U.S.C. 154(b) by 516 days.

(21) Appl. No.: 13/387,551

(22) PCT Filed: Jul. 28, 2010

(86) PCT No.: PCT/US2010/043552
§ 371 (c)(1),
(2), (4) Date: Apr. 9, 2012

(87) PCT Pub. No.: WO2011/014562
PCT Pub. Date: Feb. 3, 2011

(65) Prior Publication Data
US 2012/0190976 A1 Jul. 26, 2012

Related U.S. Application Data

(60) Provisional application No. 61/271,889, filed on Jul. 28, 2009.

(51) Int. Cl.
*A61M 31/00* (2006.01)
*A61M 25/01* (2006.01)
(Continued)

(52) U.S. Cl.
CPC ...... *A61M 25/0105* (2013.01); *A61B 17/12109* (2013.01); *A61B 17/12181* (2013.01); *A61B 17/12186* (2013.01); *A61B 19/22* (2013.01); *A61B 6/037* (2013.01); *A61B 6/507* (2013.01); *A61B 17/00491* (2013.01); *A61B 17/12022* (2013.01); *A61B 2017/00398* (2013.01); *A61B 2017/00867* (2013.01);
(Continued)

(58) Field of Classification Search
CPC ............ A61B 2017/00867; A61B 2017/1205; A61B 2019/2211; A61B 2019/2219; A61B 2019/2249; A61B 2019/5251; A61B 6/507; A61M 2025/0042; A61M 2025/0166; A61M 25/0105; A61M 25/04
USPC .............................. 604/507, 508, 19, 48, 181
See application file for complete search history.

(56) References Cited

U.S. PATENT DOCUMENTS 2,064,314 A 12/1936 Morin
2,456,451 A 12/1948 Seaver
(Continued)

FOREIGN PATENT DOCUMENTS

WO WO2008/048234 4/2008

OTHER PUBLICATIONS

Ariel, "Treatment of Inoperable Primary Pancreatic and Liver Cancer by the Intra-Arterial Administration of Radioactive Isotopes (Y99 Radiating Microspheres)," Annals of Surgery. vol. 162, No. 2 pp. 267-278 (1965).

(Continued)

*Primary Examiner* — Kevin C Sirmons
*Assistant Examiner* — Deanna K Hall
(74) *Attorney, Agent, or Firm* — Jenkins, Wilson, Taylor & Hunt, P.A.

(57) ABSTRACT

A "Smart Micro-catheter" (SMC) system comprising a device for controlled particle release and drug delivery into a blood vessel, hepatic artery or any patho-physiological target is disclosed. Methods of using the micro-catheter system for optimal targeted delivery of therapeutic microspheres comprising using subject-specific computer simulations of particle-hemodynamics are further provided.

2 Claims, 25 Drawing Sheets

(51) Int. Cl.

| | |
|---|---|
| A61B 19/00 | (2006.01) |
| A61B 17/00 | (2006.01) |
| A61B 17/12 | (2006.01) |
| A61M 25/00 | (2006.01) |
| A61M 25/04 | (2006.01) |
| A61N 5/10 | (2006.01) |
| A61B 6/00 | (2006.01) |
| A61B 6/03 | (2006.01) |

(52) U.S. Cl.
CPC ..... *A61B 2017/1205* (2013.01); *A61B 2019/2211* (2013.01); *A61B 2019/2219* (2013.01); *A61B 2019/2249* (2013.01); *A61B 2019/502* (2013.01); *A61B 2019/5251* (2013.01); *A61M 25/0068* (2013.01); *A61M 25/04* (2013.01); *A61M 2025/0042* (2013.01); *A61M 2025/0166* (2013.01); *A61N 2005/1021* (2013.01)

(56) References Cited

U.S. PATENT DOCUMENTS

| | | | |
|---|---|---|---|
| 4,095,596 | A | 6/1978 | Grayson |
| 5,355,872 | A | 10/1994 | Riggs et al. |
| 5,363,842 | A | 11/1994 | Mishelevich et al. |
| 5,404,871 | A | 4/1995 | Goodman et al. |
| 5,437,267 | A | 8/1995 | Weinstein et al. |
| 5,474,058 | A | 12/1995 | Lix et al. |
| 5,487,378 | A | 1/1996 | Robertson et al. |
| 5,843,050 | A * | 12/1998 | Jones et al. .................. 604/525 |
| 5,899,201 | A | 5/1999 | Schultz et al. |
| 5,906,202 | A | 5/1999 | Schuster et al. |
| 6,014,972 | A | 1/2000 | Sladek |
| 6,041,777 | A | 3/2000 | Faithfull et al. |
| 6,190,326 | B1 | 2/2001 | Mckinnon et al. |
| 6,202,642 | B1 | 3/2001 | McKinnon et al. |
| 6,230,703 | B1 | 5/2001 | Bono et al. |
| 6,325,475 | B1 | 12/2001 | Hayes et al. |
| 6,363,932 | B1 | 4/2002 | Forchione et al. |
| 6,422,236 | B1 | 7/2002 | Nilsson et al. |
| 6,443,146 | B1 | 9/2002 | Voges |
| 6,539,937 | B1 | 4/2003 | Haveri et al. |
| 6,682,716 | B2 | 1/2004 | Hodges et al. |
| 6,708,688 | B1 | 3/2004 | Rubin et al. |
| 6,748,945 | B2 | 6/2004 | Grychowski et al. |
| 6,830,046 | B2 | 12/2004 | Blakley et al. |
| 7,007,689 | B2 | 3/2006 | Burns |
| 7,028,686 | B2 | 4/2006 | Gonda et al. |
| 7,036,500 | B2 | 5/2006 | Niles et al. |
| 7,073,499 | B1 | 7/2006 | Reinhold et al. |
| 7,077,125 | B2 | 7/2006 | Scheuch |
| 7,080,643 | B2 | 7/2006 | Grychowski et al. |
| 7,090,830 | B2 | 8/2006 | Hale et al. |
| 7,131,441 | B1 | 11/2006 | Keller et al. |
| 7,316,360 | B2 | 1/2008 | Patel et al. |
| 7,900,625 | B2 | 3/2011 | Kleinstreuer et al. |
| 2002/0000225 | A1 | 1/2002 | Schuler et al. |
| 2002/0062062 | A1* | 5/2002 | Belson et al. ................. 600/146 |
| 2003/0089368 | A1 | 5/2003 | Zhao |
| 2003/0168057 | A1 | 9/2003 | Snyder et al. |
| 2004/0050385 | A1 | 3/2004 | Bonney et al. |
| 2004/0097805 | A1* | 5/2004 | Verard et al. .................. 600/428 |
| 2004/0133231 | A1* | 7/2004 | Maitland et al. .............. 606/200 |
| 2005/0028814 | A1 | 2/2005 | Robertson et al. |
| 2006/0137681 | A1 | 6/2006 | Von Hollen et al. |
| 2006/0149350 | A1* | 7/2006 | Patel et al. .................... 623/1.11 |
| 2006/0191534 | A1 | 8/2006 | Hickey et al. |
| 2007/0016069 | A1* | 1/2007 | Grunwald et al. ............ 600/468 |
| 2007/0044793 | A1 | 3/2007 | Kleinstreuer et al. |
| 2007/0151562 | A1 | 7/2007 | Jones et al. |
| 2007/0156042 | A1* | 7/2007 | Unal ............... 600/410 |
| 2007/0219480 | A1 | 9/2007 | Kamen et al. |
| 2007/0235029 | A1 | 10/2007 | Zhu et al. |
| 2008/0245363 | A1 | 10/2008 | Korevaar et al. |
| 2008/0262467 | A1* | 10/2008 | Humphrey et al. ........... 604/500 |

OTHER PUBLICATIONS

Asgharian, B., and Anjilvel, S., "A Monte Carlo Calculation of the Deposition Efficiency of Inhaled Particles in Lower Airways," J. Aerosol. Sci. vol. 25, No. 4 pp. 711-721 (1994).

Asgharian, B., and Anjilvel, S., "The Effect of Fiber Inertia on Its Orientation in a Shear Flow with Application to Lung Dosimetry," Aerosol Science and Technology. vol. 23, No. 3 pp. 282-290 (1995).

Atassi et al., "Multimodality Imaging Following 90Y Radio-embolization: A Comprehensive Review and Pictorial Essay," Radiographics. vol. 28, No. 1 pp. 81-99 (2008).

Balásházy et al., "Computation of Local Enhancement Factors for the Quantification of Particle Deposition Patterns in Airway Bifurcations," J. Aerosol. Sci. vol. 30, No. 2 pp. 185-203 (1999).

Balásházy et al., "Local particle deposition patterns may play a key role in the development of lung cancer," J. Appl. Physiol. vol. 94 pp. 1719-1725 (2003).

Benaïssa et al., "Modelling evaporation of multicomponent fuel droplets under ambient temperature conditions," Journal of the Institute of Energy. vol. 75, No. 502 pp. 19-26 [Abstract].

Berlemont et al., "Heat and mass transfer coupling between vaporizing droplets and turbulence using a Lagrangian approach," Int. J. Heat Mass Transfer. vol. 38, No. 16 pp. 3023-3034 (1995).

Bowes, S.M., III, and Swift, D.L., "Deposition of Inhaled Particles in the Oral Airway During Oronasal Breathing," Aerosol Science and Technology. vol. 11, No. 2 pp. 157-167 (1989).

Breedis, C., and Young, G., "The Blood Supply of Neoplasms in the Liver," Am. J. Pathol. pp. 969-984 (1954).

Broday, D.M., and Georgopoulos, P.G., "Growth and Deposition of Hygroscopic Particulate Matter in the Human Lungs," Aerosol Science and Technology. vol. 34 pp. 144-159 (2001).

Buchanan et al., "Rheological effects on pulsatile hemodynamics in a stenosed tube," Computers & Fluids. vol. 29 pp. 695-724 (2000).

Bushi et al., "Hemodynamic Evaluation of Embolic Trajectory in an Arterial Bifurcation: An In-Vitro Experimental Model," Stroke. vol. 36 pp. 2696-2700 (2005).

Campbell et al., "Analysis of the distribution of intra-arterial microspheres in human liver following hepatic yttrium-90 microsphere therapy," Phys. Med. Biol. vol. 45 pp. 1023-1033 (2000).

Cheng et al., "Dose estimate of inhaled hafnium tritide using the ICRP 66 lung model," Health Physics. vol. 82 pp. 817-824 (2002).

Fan et al., "Gass Collection Efficiency and Entrance Flow Effect of an Annular Diffusion Denuder," Aerosol Science and Technology. vol. 25, No. 2 pp. 113-120 (1996).

Fujioka et al., "Oscillatory Flow and Gas Transport Through a Symmetrical Bifurcation," Journal of Biomechanical Engineering. vol. 123 pp. 145-153 (2001).

Gemci et al., "A Numerical and Experimental Study of Spray Dynamics in a Simple Throat Model," Aerosol Science and Technology. vol. 36 pp. 18-38 (2002).

Gosman, A.D., Ioannides, E., "Aspects of computer simulation of liquid-fueled combustors," Journal of Energy. vol. 7, No. 6 pp. 482-490 (1983) [Abstract].

Grotberg, "Pulmonary Flow and Transport Phenomena," Annu. Rev. Fluid Mech. vol. 26 pp. 529-571 (1994).

Grotberg, "Respiratory Fluid Mechanics and Transport Processes," Annu. Rev. Biomed. Eng. vol. 3 pp. 421-457 (2001).

Hashimoto et al., "Quantitative Tissue Blood Flow Measurement of the Liver Parenchyma: Comparision Between Xenon CT and Perfusion CT," Dig. Dis. Sci. vol. 52 pp. 943-949 (2007).

He, C., and Ahmadi, G., "Particle Deposition in a Nearly Developed Turbulent Duct Flow with Electrophoresis," J. Aerosol Sci. vol. 30, No. 6 pp. 739-758 (1999).

Hübner et al., "Hepatic arterial blood flow velocities: assessment by transcutaneous and intravascular Doppler sonography," Journal of Hepatology. vol. 32 pp. 893-899 (2000).

Ishigami et al., "Does Variant Hepatic Artery Anatomy in a Liver Tranplant Recipient Increase the Risk of Hepatic Artery Complications After Transplantation?" AJR. vol. 183 pp. 1577-1584 (2004).

(56) References Cited

OTHER PUBLICATIONS

Joseph et al., "MEMS in the Medical World," Sensors Magazine. Apr. 1997. Jul. 19, 2008 http://archives.sensorsmag.com/articles/0497/medical/main.shtml.

Kennedy et al., "Pathologic Response and Microdosimetry of 90Y Microspheres in Man: Review of Four Explanted Whole Livers," Int. J. Radiation Oncology Biol. Phys. vol. 60, No. 5 pp. 1552-1563 (2004).

Kennedy et al., "Recommendations for Radioembolization of Hepatic Malignancies Using Yttrium-90 Microsphere Brachytherapy: A Consensus Panel Report from the Radioembolization Brachytherapy Oncology Consortium," Int. J. Radiation Oncology Biol. Phys. vol. 68, No. 1 pp. 13-23 (2007).

Kim et al., "Turbulence statistics in fully developed channel flow at low Reynolds number," J. Fluid Mech. vol. 177 pp. 133-166 (1987).

Kim, C.S., and Fiser, D.M., "Deposition Characteristics of Aerosol Particles in Sequentially Bifurcating Airway Models," Aerosol Science and Technology. vol. 31, Nos. 2-3 pp. 198-220 (1999).

Kleinstreuer C, Zhang Z, Li Z, et al. A new methodology for targeting drug-microspheres in the human respiratory system. International Journal of Heat & Mass Transfer 2008;51:5578-5589.

Kleinstreuer, C., and Zhang, Z. (2003b). Targeted drug aerosol deposition analysis for a four-generation airway model with hemispherical tumors, ASME Journal of Biomechanical Engineering, 125(2), 197-206.

Kleinstreuer, C., and Zhang, Z., "An Adjustable Triple-Bifurcation Unit Model for Air-Particle Flow Simulations in Human Tracheobronchial Airways," Journal of Biomechanical Engineering. vol. 131 pp. 1-10 (2009).

Kulik et al., "Yttrium-90 Microspheres (TheraSphere®) Treatment of Unresectable Hepatocellular Carcinoma: Downstaging to Resection, RFA and Bridge to Transplantation," Journal of Surgical Oncology. vol. 94 pp. 572-586 (2006).

Li, A., and Ahmadi, G., "Dispersion and Deposition of Spherical Particles from Point Sources in a Turbulent Channel Flow," Aerosol Science and Technology. vol. 16, No. 4 pp. 209-226 (1992).

Liu et al., "Modeling the bifurcating flow in a asymmetric human lung airway," Journal of Biomechanics. vol. 36 pp. 951-959 (2003).

Mabotuwana et al., "A model of blood flow in the mesenteric arterial system," BioMedical Engineering Online. vol. 6, No. 17 pp. 1-12 (2007).

MacInnes, J.M., and Bracco, F.V., "Stochastic particle dispersion modeling and the tracer-particle limit," Phys. Fluids A. vol. 4, No. 12 pp. 2809-2824 (1992).

Matida et al., Statistical simulation of partical deposition on the wall from turbulent.

Muller, J.H., and Rossier, P.H., "A New Method for the Treatment of Cancer of the Lungs by Means of Artificial Radioactivity," Acta radiologica. vol. 35, Nos. 5-6 pp. 449-468 (1951).

Murthy et al., "Yttrium-90 Microsphere Therapy for Hepatic Malignancy: Devices, Indications, Technical Considerations, and Potential Complications," Radiographics. vol. 25, No. 1 pp. S41-S55 (2005).

Notice of Allowance corresponding to U.S. Appl. No. 11/510,288 dated Nov. 23, 2010.

Notification Concerning Transmittal of International Preliminary Report on Patentability (Chapter I of the Patent Cooperation Treaty) corresponding to International Application No. PCT/US2006/033596 dated Sep. 4, 2008.

Notification of Trasnmittal of the International Search Report and the Written Opinion of the International Searching Authority, or the Declaration corresponding to International Application No. PCT/US2010/043552 dated Sep. 24, 2010.

Notification of the Transmittal of the International Search Report or the Written Opinion of the International Searching Authority corresponding to International Patent Application No. PCT/US2006/033596 dated Jul. 28, 2008.

Nowak et al., "Computational Fluid Dynamics Simulation of Airflow and Aerosol Deposition in Human Lungs," Annals of Biomedical Engineering. vol. 31 pp. 374-390 (2003).

Official Action corresponding to U.S. Appl. No. 11/510,288 dated Oct. 15, 2009.

Ounis et al., "Dispersion and Deposition of Brownian Particles from Point Sources in a Simulated Turbulent Channel Flow," Journal of Colloid and Interface Science. vol. 147, No. 1 pp. 233-250 (1991).

Pedley et al., "Flow and pressure drop in systems of repeatedly branching tubes," J. Fluid Mech. vol. 46, No. 2 pp. 365-383 (1971).

Pedley, "Pulmonary Fluid Dynamics," Ann. Rev. Fluid Mech. vol. 9, pp. 229-274 (1977).

Phalen, R.F., and Oldham, M.J., "Methods for modeling particle deposition as a function of age," Respiration Physiology. vol. 128 pp. 119-130 (2001).

Radeleff et al., "Acute Increase in Hepatic Arterial Flow During TIPS Identified by Intravascular Flow Measurements," Cardiovasc. Intervent. Radiol. vol. 32 pp. 32-37 (2009).

Renotte et al., Numerical 3D analysis of oscillatory flow in the time-varying laryngear.

Salem et al., "Radioembolization with 90Yttrium Microspheres: A State-of-the-Art Brachytherapy Treatment for Primary and Secondary Liver Malignancies," Journal of Vascular and Interventional Radiology. vol. 17, No. 8 pp. 1251-1278 (2006).

Sato et al., "Unresectable Chemorefractory Liver Metastases: Radioembolization with 90Y Microspheres—Safety, Efficacy, and Survival," Radiology. vol. 247, No. 2 pp. 507-515 (2008).

Shuen et al., "Evaluation of a Stochastic Model of Particle Dispersion in a Turbulent Round Jet," AIChE Journal. vol. 29, No. 1 pp. 167-170 (1983).

SM5108. Silicon Microstructures Incorporated. 2003-2004.

Tanaka et al., "Spatial and Temporal Variation of Secondary Flow During Oscillatory Flow in Model Human Central Airways," Journal of Biomechanical Engineering. vol. 121 pp. 565-573 (1999).

Thorne, "Inhalation toxicology model of endotoxin- and bioaerosol-induced inflammation," Toxicology. vol. 152, Nos. 13-23 p. 17 (2000).

Wang, Y., and James, P.W., "On the effect of anisotropy on the turbulent dispersion and deposition of small particles," International Journal of Multiphase Flow. vol. 25 pp. 551-558 (1999).

Webb et al., "Control of SMA actuators in dynamic environments," Part of the SPIE Conference on Mathematics and Control in Smart Structures, Newport Beach, California. Mar. 1999. vol. 3667 pp. 278-289.

Yu et al., "Fluid Flow and Particle Diffusion in the Human Upper Respiratory System," Aerosol Science and Technology, vol. 28, pp. 146-158 (1998).

Zhang et al., "Computational Analysis of Micron-particle Deposition in a Human Triple Bifurcation Airway Model," Computer Methods in Biomechanics and Biomedical Engineering. vol. 5, No. 2 pp. 135-147 (2002).

Zhang, Z., Kleinstreuer, C, Donohue, J.F. and Kim, C. S. (2005). Comparison of Micro- and Nano-Size Particle Depositions in a Human Upper Airway Model, Journal of Aerosol Science, vol. 36, 211-233.

Zhang, Z., Kleinstreuer, C. and Kim, C.S. (2002f). Gas-Solid Two-Phase Flow in a Triple Bifurcation Lung Airway Model, Int. J. Multiphase Flow, vol. 28, pp. 1021-1046.

* cited by examiner

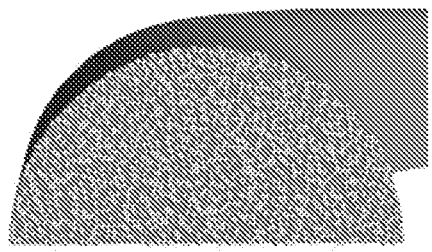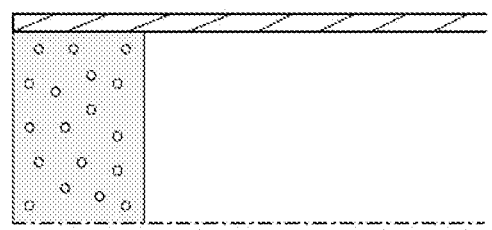
Fig. 5(a)
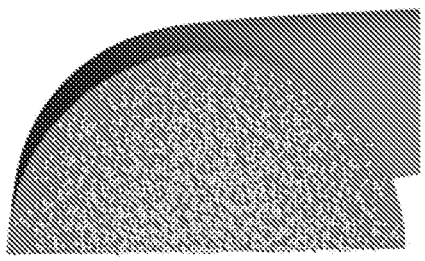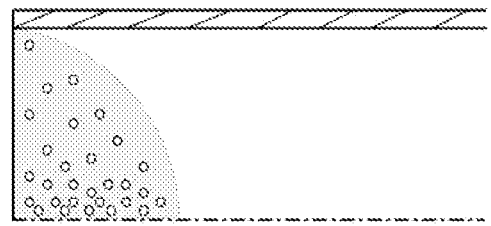
Fig. 5(b)

Mock Hepatic Experimental Model

METHODS AND DEVICES FOR TARGETED INJECTION OF MICROSPHERES

RELATED APPLICATIONS

This application claims the benefit of U.S. Provisional Patent Application Ser. No. 61/271,889, filed Jul. 28, 2009, the disclosure of which is incorporated herein by reference in its entirety.

TECHNICAL FIELD

The presently disclosed subject matter relates to micro-catheter systems. In particular, the presently disclosed subject matter relates to micro-catheter systems capable of producing a controlled injected microsphere stream which can be directed to a desired patho-physiological target area while minimizing deposition of microspheres on healthy tissues.

BACKGROUND

A significant cause of death from cancer is uncontrolled disease from metastatic cancer. This results in significant suffering and eventual death in hundreds of thousands of patients worldwide each year. Liver cancer is the sixth most common cancer in the world and the third leading cause of cancer related death (Parkin 2005). For instance the World Health Organization (WHO) reported that in 2006 hepatic metastases from colorectal cancer alone claimed more than 800,000 lives while another 662,000 died from hepatoma.

Surgical resection is the preferred, and presently most effective, treatment approach for primary and metastatic liver malignancies; however, 80 to 90% of patients are precluded from surgical intervention due to tumor size, location, or complexity (Ibrahim 2009, Welsh 2006). Depending on cancer tumor characteristics, alternative treatment options include full body chemotherapy, ablative therapies, trans-arterial embolization (TAE), trans-arterial chemo-embolization (TACE), radiation therapies, the newly developed radioembolization (RE) treatment, jet-injection of gel-like chemotherapy drugs, or a combination of radioactive microspheres and chemo-drug (i.e., RE plus TACE). Chemotherapy treatments are effective for the many cancer types; however, the liver remains an area of tumor persistence (Kennedy, 2004), with more than 50% of patients with solid tumors experiencing full resistance to chemotherapy (Welsh et al., 2006).

TAE techniques capitalize on the unique anatomic and pathologic features of liver tumors. Among the many established and evolving techniques for treating liver cancer that are not related to chemotherapy is hepatic arterial particle delivery—with or without radiation embedded in the particles. The liver possesses a dual blood supply; portal venous blood supplies at least 75% of the normal liver requirements while the hepatic arterial vessels provide only a small amount of blood to normal parenchyma but, nearly 100% of the required blood flow to metastatic and primary cancers in the liver. Furthermore, there are a higher number of hepatic arterial vessels surrounding the tumor site compared to normal liver tissue (Kennedy 2004). This dual blood supply can be used to a therapeutic advantage. Any microspheres released into the hepatic artery can preferentially reach the tumor as opposed to normal tissue. Additionally, larger sized microspheres (>10 μm) will become permanently lodged in hepatic vessels, as they are too large to pass through the capillary bed (8-10 μm) and into circulation. Over the past 40 years the anatomic advantage of the dual blood supply has been exploited with increasing success using the hepatic artery in two ways: (i) to mechanically block blood flow and (ii) to implant radioactive microspheres on tumors.

The first method is to deliver bland (i.e. non radioactive) microspheres (typically 100-300 microns diameter) with or without chemotherapy to mechanically block blood flow to tumors causing destruction via ischemia and high concentrations of chemotherapy. With traditional TAE, bland microspheres are delivered into the hepatic arteries destroying tumors via ischemia. However, liver tumors are highly vascularized, with the ratio of tumor vessels to normal-tissue vessels estimated to be 3:1, decreasing the efficacy of this singular approach. Combination treatments have been developed, including TACE, where high dosages of chemotherapy alongside microspheres are introduced directly into the hepatic arteries. Due to the localized delivery, the chemotherapy drugs have a greater impact than with full body therapies.

The second method, brachytherapy, uses radioactive (usually $^{90}Y$) microspheres (typically 20-35 microns diameter) which implant permanently and preferentially in the terminal arterioles of tumors. Contrary to chemotherapy, radiation therapy has consistently demonstrated efficacy in treatment of liver tumors. Native liver tissue, however, has a lower tolerance to radiation than tumor tissue or adjacent organs, limiting the usage of external radiation therapies. In recent years, embolization procedures utilizing radioactive microspheres for localized treatment of liver tumors have surfaced with promising results. Microspheres (20-40 μm in diameter) infused with a radioactive isotope (usually $^{90}Y$) are injected into the hepatic arteries and implant permanently and preferentially in the terminal arterioles of tumors (Kennedy et al., 2004; Welsh, 2006; Salem & Thurston, 2006a-c). $^{90}Y$ microspheres emit low doses of radiation with high energy, but low penetration (d90=2 mm), maximizing the effect on tumor tissue while leaving most normal liver parenchyma unharmed (Kennedy, 2004).

Despite some success to date with both mechanical blocking and brachytherapy approaches, more detailed information about and discovery of important factors influencing micron particle transport in the hepatic arterial system is needed to improve treatment.

The hepatic artery is 6 mm in diameter and its daughter vessels collapse to 1.2 mm. Beyond the daughter vessels are capillaries which get smaller than the diameter of microspheres. The microspheres have to be released upstream because the catheter itself, is between 1.5-2 mm in diameter. It can hardly be inserted in the daughter vessels without rupturing them, let alone into the capillaries which supply the nutrients to the tumors.

The effectiveness of a cancer therapeutic methodology or device can be measured by its ability to reduce or even eliminate tumors without damaging healthy tissue. Effective treatments can require a high-percentage of drug deposition at specific sites, such as tumors, or in desired regions. Some drugs are so aggressive and/or expensive that targeted delivery is imperative.

Existing drug delivery devices, however, exhibit poor target deposition efficiencies. Consequently, significant portions of the often-aggressive and expensive therapeutic agent used to combat diseases such as cancer can deposit on healthy tissue. Thus, there is a need in the art for improved microsphere delivery devices, especially delivery devices that can target specific patho-physiological areas in the body.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. The phrase "and/or" can mean either "and" or "or," in other words one or more of the stated cases can occur. To avoid excessive repetition, this Summary does not list or suggest all possible combinations of such features.

In some embodiments of the presently disclosed subject matter, a method of delivering an active agent to a patho-physiological target area of a body of a subject in need thereof is provided. In some embodiments, the method comprises providing a "Smart Micro-catheter" (SMC) system for directing to a subject a controlled stream comprising an active agent and regulating a release position of the active agent to deliver the active agent to a patho-physiological area of the subject, such as but not limited to a target area of the subject's liver. In some embodiments, the method comprises employing a patient specific computer simulation to predict particle blood flow, wherein the simulation uses back-tracking to record the position from where a particle landing on the target was released.

In some embodiments, the method comprises using single photon emission computed tomography (SPECT) or nuclear magnetic imaging to detect where the active agent lands within the subject.

In some embodiments, the active agent comprises microspheres and/or drugs. In some embodiments, the active agent comprises one or more physical characteristics selected from the group including but not limited to: a particle size of from about 1 µM to about 40 µM; a substantially spherical shape; and a low density.

In some embodiments, the SMC device comprises a SMC with an adaptive nozzle, which can be inserted in the blood vessel, such as in the hepatic artery. The flexible nozzle can be made stationary by manual adjustment or the use of actuators, for example, shape-memory-alloy wires.

In some embodiments of the presently disclosed subject matter, a SMC device for targeted release of an active agent is provided. In some embodiments, the SMC device, in flow communication with an injection system, comprises: a tube having an inlet at one end, an outlet at an opposing end, and a wall joining the inlet and the outlet; an adaptive nozzle that can be positioned within a blood vessel having a nozzle inlet engaged with the tube outlet and a nozzle tip outlet distal to the tube outlet, wherein the nozzle tip outlet and the nozzle inlet are in flow communication and adapted for passage of a stream therebetween; and one or more actuators operationally linked to the adaptive nozzle, wherein the one or more actuators can position the nozzle tip outlet and thereby regulate the stream release from the SMC device.

In some embodiments the one or more actuators can slidingly position the nozzle to vary its alignment with the blood vessel wall.

In some embodiments, the one or more actuators comprise an active material, such as for example an active material selected from the group including but not limited to a shape memory alloy (e.g., an alloy of nickel and titanium), a shape memory polymer, a magnetostrictive material, and a piezoceramic material.

In some embodiments, the actuators are insulated with a biocompatible polymer sheath.

In some embodiments, the SMC device comprises one or more micropressure sensors positioned proximal to the tube outlet or nozzle. The sensors can detect distance from a blood vessel wall and transmit a signal to the actuators. The actuators can vary the position of the nozzle to change the alignment in response to the signal. The signal from the micropressure sensors can be transmitted to a control logic (e.g. a proportional-integral-derivative (PID) algorithm), which interprets the signal and transmits an actuator control signal to the actuators. In some embodiments, the control logic is in operational communication with computational fluid-particle dynamics results that determine the desired position of the adaptive nozzle to direct the stream to a desired target area in the body of a subject.

In some embodiments, the SMC device comprises one or more microprocessor sensors which can sense resistance in the actuators. A signal from the microprocessor sensors is transmitted to the control logic which interprets the signal and transmits a signal to control the actuators. The actuators receive the signal and vary the position of the nozzle to change the alignment of the nozzle in relation to the blood vessel.

In some embodiments, the catheter tip is positioned by electromagnetic tracking.

In some embodiments, the adaptive nozzle comprises a flexible polymer that permits flexing of the adaptive nozzle. In some embodiments, the one or more adaptive nozzle actuators comprise a first set of adaptive nozzle actuators that position the nozzle tip outlet and a second set of adaptive nozzle actuators that flex the adaptive nozzle such that the nozzle tip outlet is axially aligned with the blood vessel axis after positioning. The one or more adaptive nozzle actuators can comprise an active material, such as for example a shape memory alloy (e.g., an alloy of nickel and titanium), a shape memory polymer, a magnetostrictive material, or a piezoceramic material.

In some embodiments, a doctor or operator manually inserts the SMC with the aid of constant CT scans to reach the predetermined axial position. The SMC device can then be radially positioned using manual, mechanical, and/or electromechanical operation, as examples.

In some embodiments, the SMC device is radially positioned for desired release of active agent via manual operation with the aid of sensor feedback.

In some embodiments, the SMC device is mechanically operated to achieve the optimal radial position. The SMC device can comprise push/pull rods, support or tripod legs, and actuators that can be deployed to anchor the SMC in place.

In some embodiments, the SMC device comprises actuators that are antagonistic to each other, thereby providing two way motion of the tripod legs.

In some embodiments, the SMC device is electro-mechanically operated to achieve the desired radial position. The SMC device can further comprise one or more stent rings with adjustable tripod struts and shape memory alloy (SMA)-wires folded in the nozzle area. The tripod struts or SMA-wires are deployed by electric current to position the nozzle and nozzle tip according to the predetermined coordinates via a feedback control loop based on position sensor signals and a subject-specific microprocessor program.

In some embodiments, the active agent is released in a uniform distribution.

In some embodiments of the presently disclosed subject matter, a SMC system for targeted release of a stream of active agent is provided. In some embodiments, the SMC system comprises: a source of active agent; an injection system in flow communication with the source of active agent; and a SMC device in flow communication with the injection system. The SMC device can in some embodiments comprise: a tube having an inlet at one end, an outlet at an opposing end, and a wall joining the inlet and the outlet; an adaptive nozzle positioned within the interior of the tube and having a nozzle inlet engaged with the tube outlet and a nozzle tip outlet distal to the tube outlet, wherein the nozzle tip outlet and the nozzle inlet are in flow communication and adapted for passage of a stream therebetween; and one or more actuators operationally linked to the adaptive nozzle, wherein the one or more actuators can position the nozzle tip outlet and thereby target stream release from the SMC device.

In some embodiments, the injection system comprises a computer-controlled syringe pump or similar automated active agent delivery device. The computer-controlled syringe pump can be time-controlled.

In some embodiments, an injection system comprises a controllable reservoir chamber having an inlet in flow communication with the source of active agent and an outlet in flow communication with the SMC device. In some embodiments, the injection system comprises: a pressure sensor that measures pressure within the controllable reservoir chamber; an inlet valve for controlling entry of a active agent into the controllable reservoir chamber through the reservoir chamber inlet; and an outlet valve for controlling release of the active agent from the controllable reservoir chamber through the reservoir chamber outlet, wherein the pressure sensor measures pressure within the reservoir chamber and regulates opening and closing of the inlet valve and the outlet valve in order to maintain a desired pressure within the reservoir chamber. In some embodiments, the inlet and outlet valves each comprise an active material actuator, such as for example a thin film actuator. In some embodiments, the active material actuator comprises an active material selected from the group including but not limited to a shape memory alloy, a shape memory polymer, a magnetostrictive material, and a piezoceramic material.

Accordingly, it is an object of the presently disclosed subject matter to provide a SMC system for targeted delivery of active agent. This object is achieved in whole or in part by the presently disclosed subject matter.

An object of the presently disclosed subject matter having been stated above, other objects and advantages will become apparent to those of ordinary skill in the art after a study of the following description of the presently disclosed subject matter, figures, and non-limiting examples.

BRIEF DESCRIPTION OF THE DRAWINGS

(FIG. 1a) representative image of biological case study of hepatic blood vessel with tumor (TU); (FIG. 1b) representative hepatic artery with major branch vessel (BRV) and four daughter vessels (1, 2, 3, 4). The direction of inflow (IF), particle injection plane (PIP), parent vessel (PV), and tumor vessel branch (TVB) are also depicted.

FIG. 2a shows the geometry including outlet 1 (1) and outlet 2 (2). $\Theta_1=\Theta_2=45°$. The diameter (D) of outlet 2 is two-thirds that of $D_0$. The diameter of outlet 1 is equal to $D_0$. FIG. 2b shows the comparison between experimental and computational results. Flow Ratio (Q1/Q2) (X-axis) is plotted against the Exit Fraction (%) (Y-axis). Q1 and Q2 are the flow through Outlets 1 and 2, respectively. Results from Bushi et al. (2005) for outlet 1 (squares, B1) and outlet 2 (triangles, B2) and numerical results for outlet 1 (solid line, N1) and outlet 2 (dashed line, N2) are shown.

(FIG. 3a) branch-outlet (BRV) pressure ($P_B$) equal to the daughter-outlet pressure ($P_D$); (FIG. 3b) branch-outlet pressure 20% over the daughter-outlet pressure. PV=parent vessel. TVB=tumor vessel branch.

(FIG. 4a) global flow rate distribution, i.e., percentage of total blood flow exiting the branch vessel (BRV; right bars) or the sum (DS) of all four daughter vessels (left bars); (FIG. 4b) local flow rate distribution, i.e., percentage of incoming blood flow exiting individual daughter vessels 1, 2, 3, and 4. The two scenarios from FIG. 3a-3b are shown: $P_B$ $P_D$ (dark bars), $P_B=1.2P_D$ (lighter bars).

FIGS. 5a-5b are diagrams showing simulations of microsphere particle distributions at the inlet of the main hepatic artery presented in FIGS. 1a and 1b: (FIG. 5a) uniform, i.e., equally-spaced particle concentration; (FIG. 5b) parabolic distribution with a higher particle concentration around the center-line. In both figures, the normal plane view is shown on the left and the axial particle concentration profile is shown on the right.

FIG. 17a shows a transient particle release map and spatial release positions of injection during accelerating time zone (area between dots in right panel). FIG. 17b shows the particle trajectories for specific daughter vessel targeting. Daughter vessels 2 and 4 are targeted in the left and right panels, respectively. The injection position (dots in circle) is shown in the cross-sectional (semi-circle) drawing below each hepatic arterial system drawing. CHA=common hepatic artery. GDA=gastroduodenal artery. IP=injection position.

FIG. 19a) overview, FIG. 19b) magnified view of SMA "tendons" 1910; and FIG. 19c) selective placement of the catheter (SMC) within the vessel's cross section. 1902=catheter legs. 1904=blood vessel. 1906=nozzle. 1908=catheter body. Sh=sheath.

FIG. 21a shows a computational particle release map indicating the theta angle by shading and the experimental particle release position (in circle, RP). The inlet Reynolds number was approximately 600. The release positions for branch vessel (BRV) and daughter vessels (1, 2, 3, and 4) are shown with different symbols. FIG. 21b is photograph of a mock hepatic experimental model (see FIG. 20), targeting both daughter vessels 1 and 2 (dark regions indicate microsphere deposition (MD)). FIG. 21c shows the percentage of microspheres deployed by branch when the second daughter branch 2 was targeted. FIG. 21d shows the repeatability of results (from a different release point than in FIG. 21c) for percentage of microspheres deployed (Y-axis) by branch (X-axis) for consecutive runs.

DETAILED DESCRIPTION

The methodology and device of the presently disclosed subject matter are applicable for desired and ideally optimal drug delivery to any patho-physiological target in the body. Achieving up to 100% mechanical delivery of microspheres and/or drugs onto tumors, including solid tumors, (for example, liver tumors), or optimal drug-targeting onto any other malignancy or patho-physiological area in the organ system provides advantages in terms of saving lives, minimizing side-effects, and lowering costs. This technology and procedural methodology have the potential to transform RE by offering unprecedented control of microsphere deployment (or delivery of drug compositions such as drug-ethiodol-mixture) for the treatment of a variety of cancers including but not limited to colorectal, hepatocellular, neurendocrine, breast and prostate.

The determination of suitable particle release positions for desired site-specific targeting is an aspect of the presently disclosed subject matter, and can be achieved via a process labeled "backtracking". The particular emission positions of microspheres and/or drugs that enter different regions or land on different targeted sites can be determined via backtracking, which involves recording from where a particle landing on or surrounding a tumor was released. In order to simulate and analyze microparticle transport in the circulatory system, realistic blood vessel models, flow domain meshes, blood flow and particle trajectory equations as well as an accurate and robust equation solver were employed. In some embodiments, a representative replica of the human hepatic artery was employed wherein different particle release positions resulted in controlled concentrations at desired daughter vessel exit locations.

The particular positions of particles that exit the SMC's nozzle or land on different targeted sites were determined via backtracking. Then particles were released at the desired exit or deposition locations. Particles released from different fixed points, as can be achieved with a controlled nozzle, can enter different parts of the blood vessel. The nozzle can be positioned at a particular angle so that most if not substantially all of the released particles can reach the desired target section.

Detailed published reports are available regarding the current state of the art in $^{90}$Y-microsphere treatment, patient selection, techniques, toxicity and clinical outcomes and are not discussed here except in brief summary.

Figure 9:
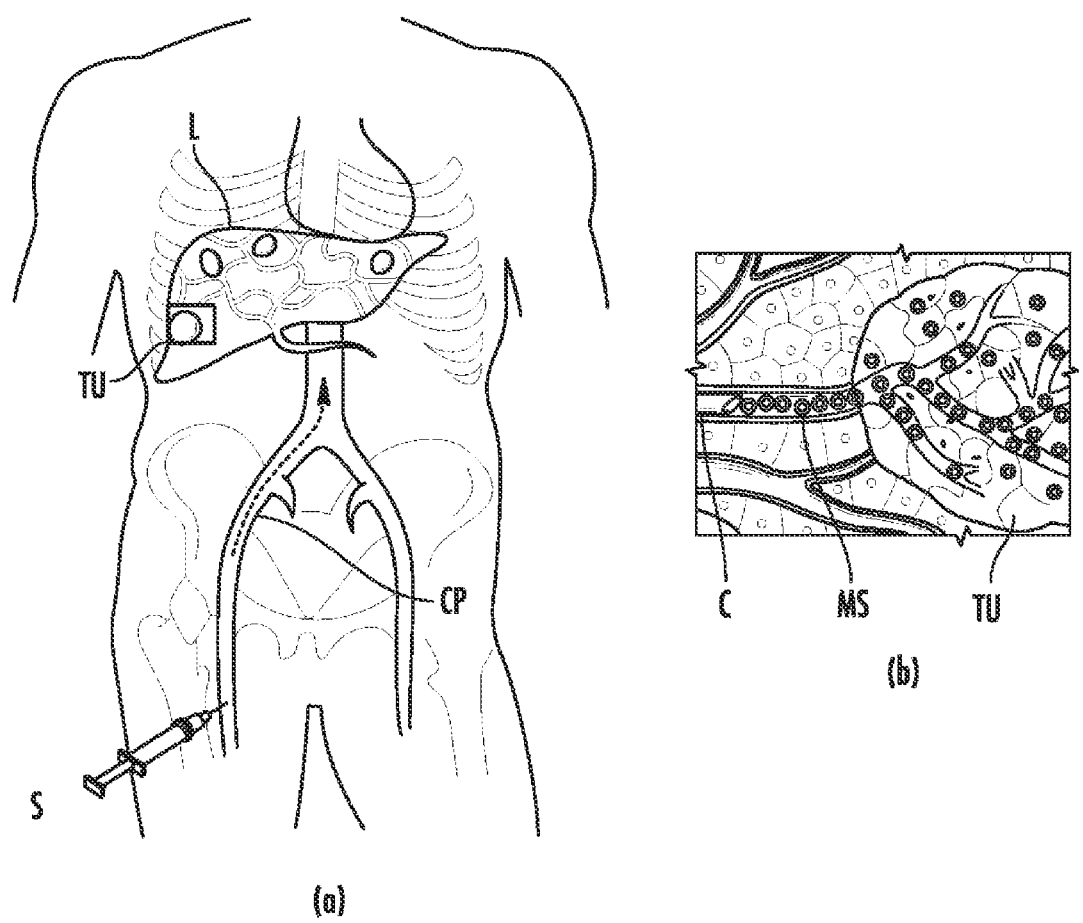
FIGS. 9a-9b are diagrams of catheter insertion into the hepatic artery of a patient with liver tumors (TU) (left panel) and existing techniques for delivering $Y^{90}$ microspheres (MS) to a tumor using a basic catheter (C) resembling a drinking straw at its tip (right panel). L=liver. CP=catheter passageway. S=syringe.

Current micro-catheter (MC) systems can at best broadly target regions of the body, such as the hepatic artery. Under methods in use today, radioactive microspheres, such as $Y^{90}$, or other micro-drugs are injected into blood vessels such as the hepatic artery via a basic micro-catheter, such as a single-lumen catheter, positioned near the tumor site. The device is primitive, a tiny tube with a straight tip without a nozzle, analogous to a cut soda straw. See C in FIG. 9b. Referring further to FIGS. 9a-9b, micro-catheter C is inserted in hepatic artery, via the catheter passageway CP. At the inlet end is a reservoir of radioactive microspheres MS (and/or drugs in some embodiments). Using a standard manually-operated syringe S, in a hit and miss type of operation, the physician releases radioactive microspheres MS into the bloodstream and hopes that the majority of them hit tumor TU. The microspheres MS that hit tumor TU destroy tumor cells through their locally emitted radiation. This delivery is non-directional. The MC has no sensors for determining radial position. No positioning is performed other than to avoid hitting the arterial wall with the micro-catheter C as it is snaked in. Microspheres that miss the tumor might destroy tissue of healthy liver L or, even worse, get into other parts of the body (e.g. migrate to other parts of the body, such as from the liver to the intestines) and then destroy other organs, either via ischemia or radiation damage. They might even get into the intestinal system and cause damage all over the subject's body.

Another consideration is that physical size constraints limit the catheter placement to just beyond the hepatic branch for left and right hepatic arteries, which allows only the selection of the left or right lobe of the liver for microsphere delivery. The catheter requires periodic verification of placement during the procedure, as the catheter tip can work itself free of the targeted artery. Additionally, if the flow into the capillary bed becomes slower than the microsphere injection rate, as can be the case when the capillaries fill with microspheres, the injected microspheres can reflux out of the desired artery and into neighboring arteries and branches of the common hepatic artery. Any microspheres that reach sensitive organs such as the stomach or duodenum can cause mucosal edema and ulceration. Abnormal vessel shunting can also result in microsphere migration to non-target organs. Common causes of improper microsphere injection include inadequate delivery volume, infusion speed, and catheter placement too close to gastric or gastroduodenal feeding vessels (Welsh, 2006). Despite some success to date with particle delivery from the hepatic arteries, the lack of ability to directly target the tumor site has limited the advancement of these treatments for liver tumors.

Assuming the oncology need is demonstrated, eligibility for microsphere treatment, in the case of liver cancer, is mainly dependent upon adequate liver reserve and access to the hepatic artery. Most patients are considered for microsphere therapy as salvage after they have received multi-agent chemotherapy and anti-angiogenesis agents for months. Others have undergone multiple liver surgeries and procedures i.e. radiofrequency ablation, bland embolization, chemo-embolization and stereotactic radiotherapy. Thus sparing the remaining healthy liver is a top priority while simultaneously implanting sufficient radiation to destroy persistent tumor deposits. The presently disclosed subject matter can play a role in transforming RE therapy from its current Level 4 tumor-treatment ranking to the most preferred option after surgery. Physical indices of $^{90}Y$-microspheres are known and were used to develop the model explained below.

The presently disclosed subject matter provides a SMC system, which can in representative embodiments fulfill two tasks simultaneously: the provision of substantially maximum drug particle deposition on desired target sites and the minimization of deposition of potentially very aggressive drugs on healthy tissue. These tasks are achieved by the targeted release of a microsphere and/or drug stream from the SMC system. The presently disclosed SMC systems provide for targeting regions in specific daughter branches of a blood vessel. Together with drastically minimized deposition on other healthy tissue, the presently disclosed SMC systems can provide safer and more efficient treatment of cancer and other diseases through targeted drug delivery. In addition, the system also creates a platform for the intake of various other kinds of therapeutic agents with desirable efficiency. The presently disclosed subject matter can increase the efficacy and safety of RE and potentially expand the number of patients eligible for the procedure; thus, reducing the number requiring chemotherapy.

In contrast to conventional RE approaches described above, the presently disclosed subject matter uses computational fluid-particle dynamics (CF-PD) analysis to predict a correlation between microsphere and/or drug stream release position into a bloodstream and the downstream deposition location of the microspheres and/or drugs. Consequently, targeted delivery can be achieved by controlling the particle release positions. In some embodiments, the presently disclosed subject matter can address control of the particle release positions utilizing a SMC system of the presently disclosed subject matter for targeted delivery of an active agent in a microsphere and/or drug stream.

Backtracking

A goal of the presently disclosed subject matter is optimal targeting where most if not all of the radioactive microspheres and/or drugs deposit on tumor cells and kill the tumor through release of radioactivity. In a procedure termed "backtracking," subject-specific computer simulations of blood-particle flow were employed in which the optimal release positions of all microparticles that landed on the tumor or pathological region of interest were recorded. A map of the positions was created. From this microsphere-release-position map, the injection location of radioactive particles (or encapsulated biochemical drugs) is determined to achieve up to 100% tumor-deposition efficiency in some cases. Sites within the human body are selectively targeted using CF-PD simulations of human fluid passageways. These simulations predict the necessary radial and axial SMC position-coordinates for optimal microsphere and/or drug release within the common, right and/or left hepatic arteries (i.e., location of injection-point is case-dependent) for targeting of specific daughter branches leading to tumor sites (see FIGS. 17a and 17b). The computationally predetermined drug-microsphere stream characteristics and release positions are a function of a subject's blood vessel morphology, type of drug, and deposition site. As used herein, the term "subject" refers to both human beings and animals (e.g., mammalian subjects) for medical, veterinary, testing and/or screening purposes.

In some embodiments, medical images of the subject are obtained via CT scan. The images are in the form of Digital Imaging and Communications in Medicine (DICOM) files and are translated into geometry files for the computer simulation. These provide the positions of the blood vessels and tumor(s). This information is used together with the pressure level and blood flow for the particular subject to determine the optimal release position of the microspheres and/or drugs. Using the exact geometry and blood flow of the subject, which is on the computer in transient 3D, simulations of microsphere and/or drug releases are performed from different accessible positions. Thousands of microspheres and/or drug particles are released via computer simulation and their travel paths through the daughter vessels and where they ultimately deposit are recorded. By backtracking along the paths of the microspheres and/or drugs that land on the target, the optimal release position(s) can be determined. The nozzle of the catheter is moved to that position in the subject for release of the actual microspheres and/or drugs at the right point in time of the blood flow, resulting in the microspheres and/or drugs landing on the target.

Figure 7:
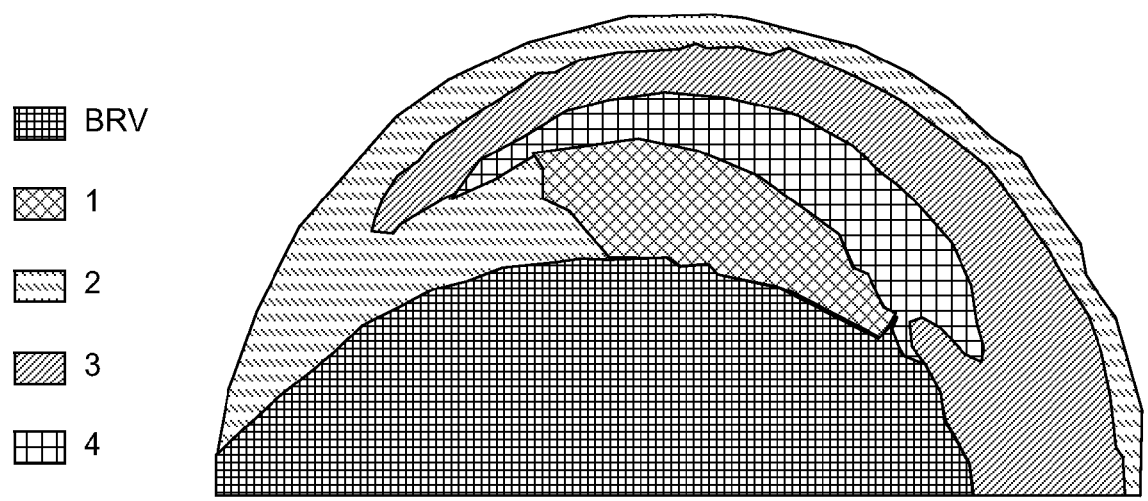
FIG. 7 is a cross-sectional diagram showing the simulated release positions of microspheres at the particle injection plane (see FIG. 1a) for particles reaching the five outlet branches presented in FIGS. 1a and 1b (upper half cross-sectional area shown). BRV=branch vessel. Daughter vessels=1, 2, 3, and 4.
Figure 10:
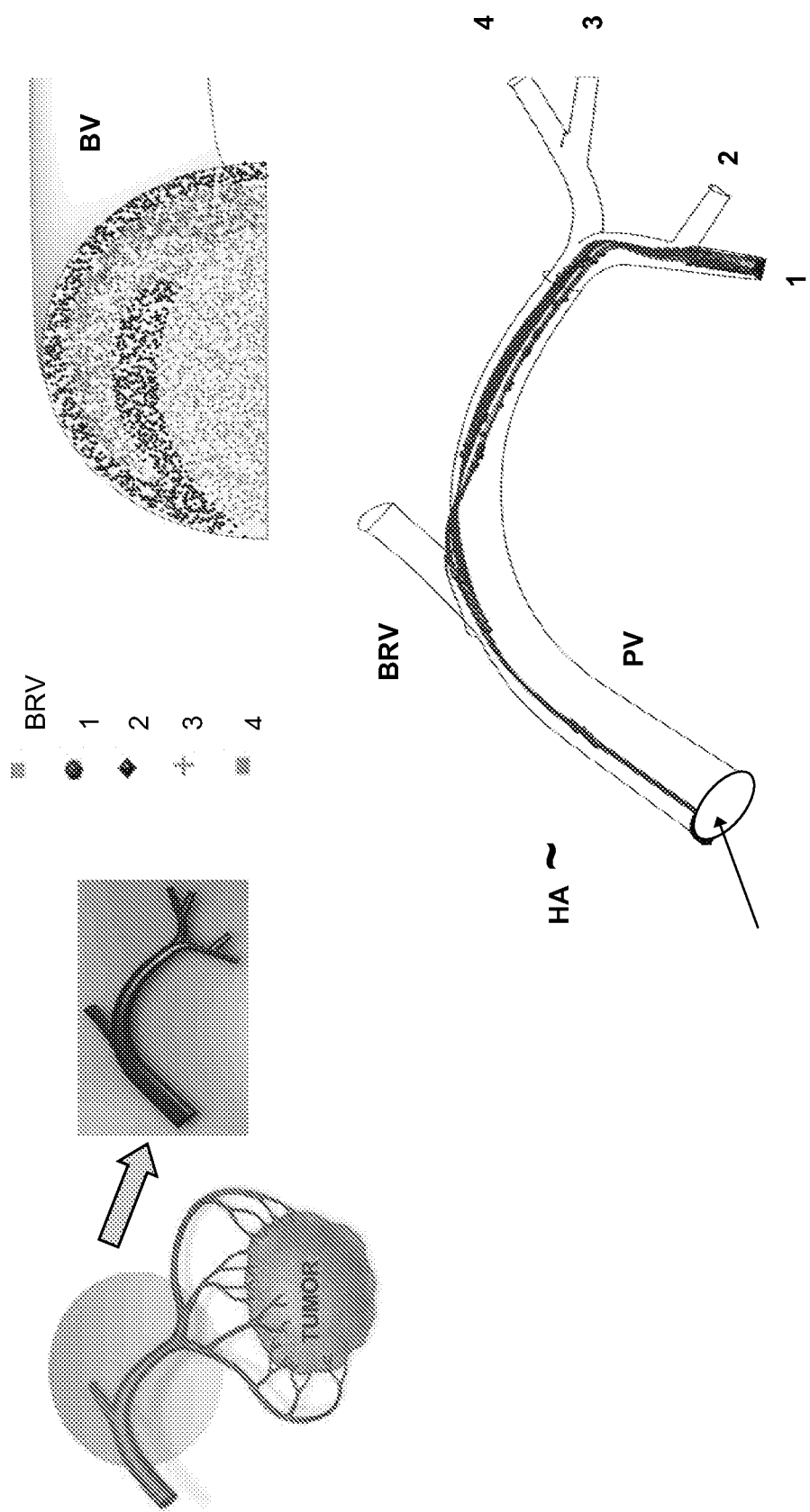
FIG. 10 is a diagram of biological-inspired computational modeling of hepatic arteries (HA) used to predict the path of injected particles, corresponding to that presented in FIGS. 1a-1b. The process enables targeting the specific daughter vessel(s) (1, 2, 3, 4) leading to a tumor (TU). The bottom right panel is a computer simulation showing half of the pseudo-circular blood vessel. The arrow in the release plane points to the position of the tip of the catheter's nozzle. PV=parent vessel. BRV=branch vessel.

In the diagram of a subject's hepatic artery system in FIG. 10, the path of injected particles is predicted via biological-inspired computational modeling of hepatic arteries. This allows the targeting of specific daughter vessels leading to the tumor. Microspheres and/or drugs released from particular departure areas travel to the branch or daughter vessel exit indicated in the diagram. For example, shown in the computer simulation in the bottom right panel, microspheres and/or drugs released in the area of the hepatic artery depicted in the inlet plane by rectangle symbols (See also area of diagonal lines in FIG. 7) travel to Daughter vessel 4 and deposit on any tumors served by that blood vessel.

Figure 6:
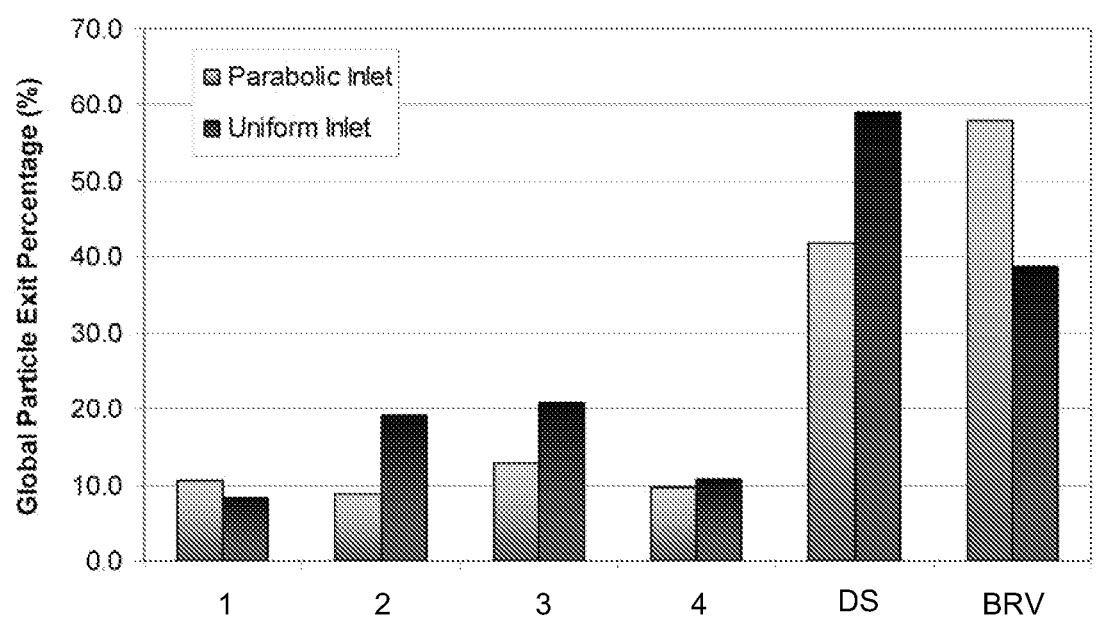
FIG. 6 is a graph showing global exit percentages of microsphere particles at the bifurcation branch (BRV) and four daughter (1, 2, 3, 4) vessels presented in FIGS. 1a and 1b resulting from uniform (dark bars) and parabolic (lighter bars) inlet distributions. "Global particle exit-percentage" is the number of particles exiting a specific vessel divided by the total number of particles injected. Comparative exit percentages are also shown for the sum of the four daughter vessels (DS).

If the location where individual particles exit is known, their release positions in the injection plane can be determined via backtracking as illustrated in FIG. 6 for the case of the uniform particle inlet distribution. If a tumor would be solely serviced by daughter vessel 1, microspheres (e.g. $^{90}$Y-microspheres) and/or drugs could be delivered via a catheter well-positioned in the above-center location of the injection cross-section, as indicated with circles in FIG. 7.

Desirable and even optimal injection/SMC-tip locations are obtained via the computational "backtracking" strategy. During the process, microparticle loads are randomly initialized (uniformly distributed across, for example, the common hepatic artery (CHA) cross section) and their trajectories simulated. Those microspheres and/or drugs depositing on the target site (i.e., a tumor) are back-tracked to establish a particle-release map which correlates specific release zones with specific target sites/regions (See e.g. FIGS. 17a and 17b). In activating overlapping release zones, more than one daughter vessel can be targeted.

Figure 17A:
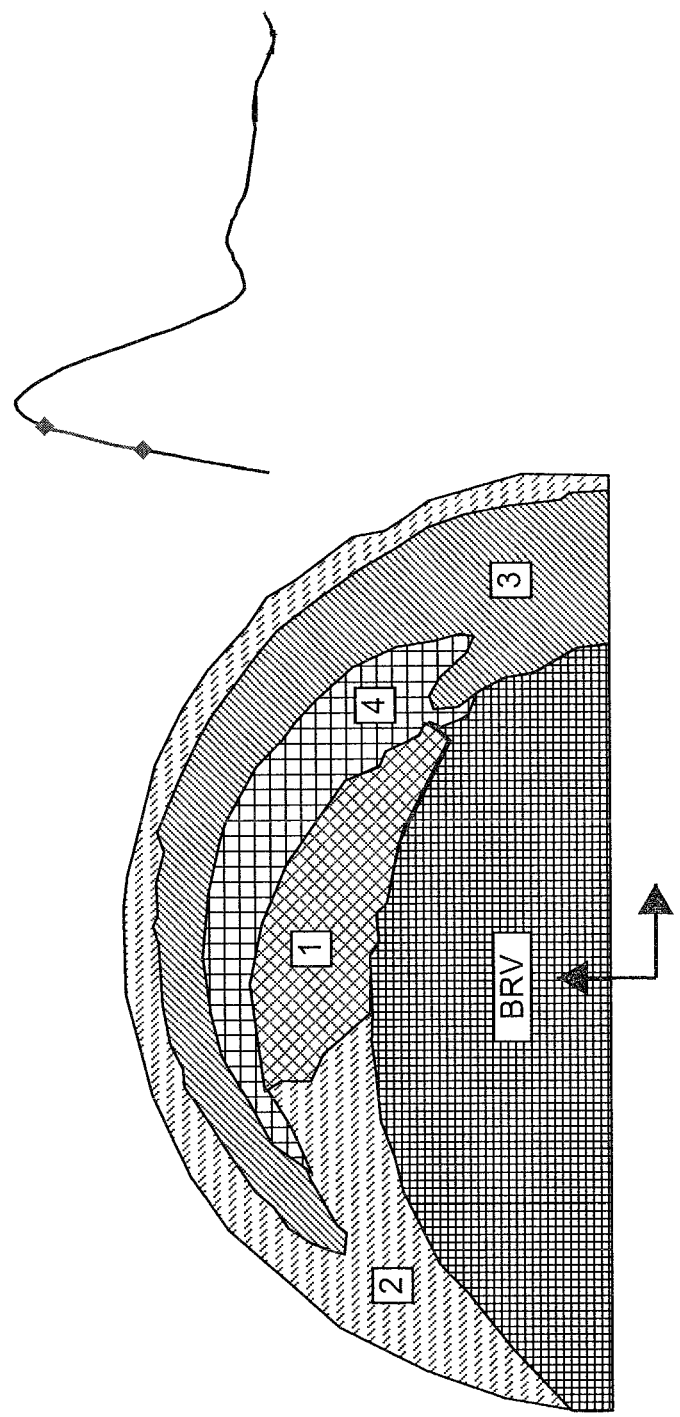
FIGS. 17a and 17b are diagrams showing determination of optimal release sites.
Figure 18:
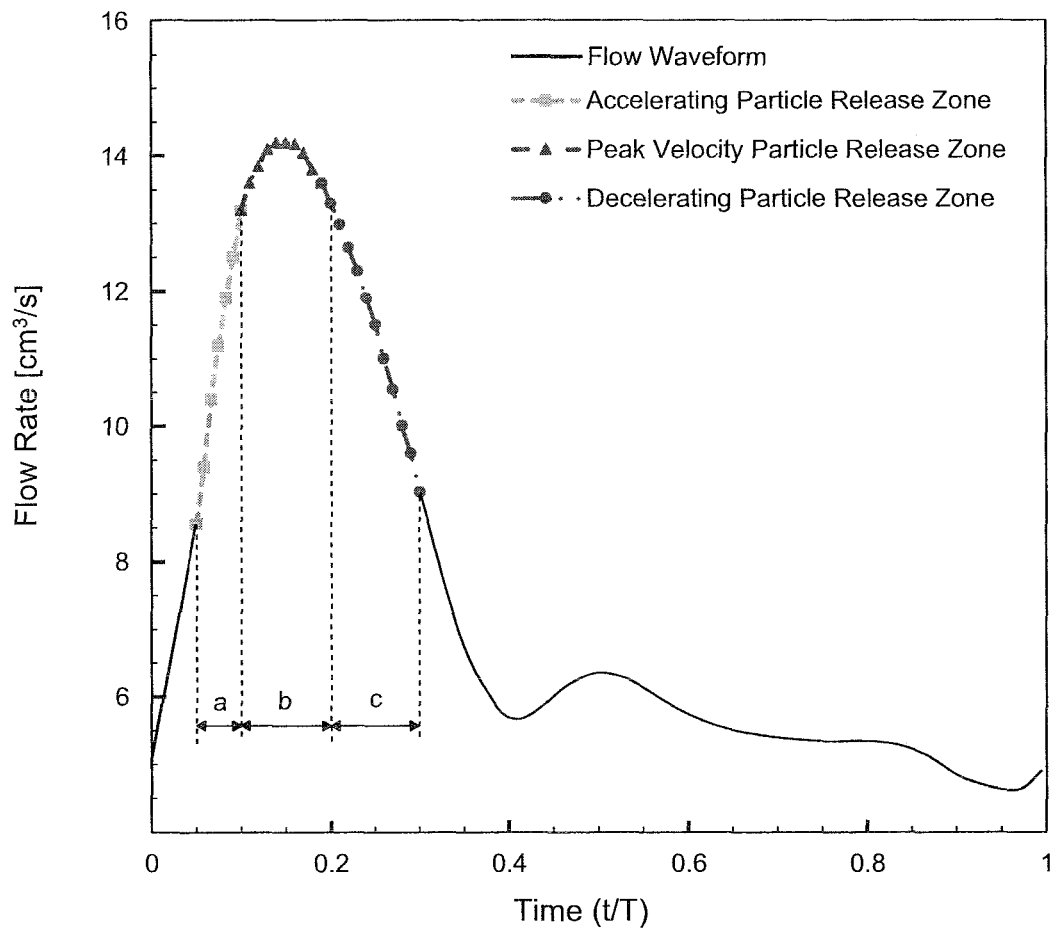
FIG. 18 is a graph of a typical cardiac cycle showing the three time periods for which particle-release maps are computed. The flow waveform is shown as a solid line. The accelerating particle release zone (a) is shown as a dotted line with square symbols. The peak velocity particle release zone (b) is shown as a line with alternating dots and dashes with triangle symbols. The decelerating particle release zone (c) is shown as a line with dashes separated by two dots with circle symbols.

These computations consider the effects of transient blood flow (e.g. the pulsatile flow associated with the cardiac cycle, FIG. 18). Particle release maps have been calculated for three different time periods within the cardiac cycle, one of which, the accelerating time zone, is shown in FIG. 17a.

Axial and Radial Positioning

Figure 11:
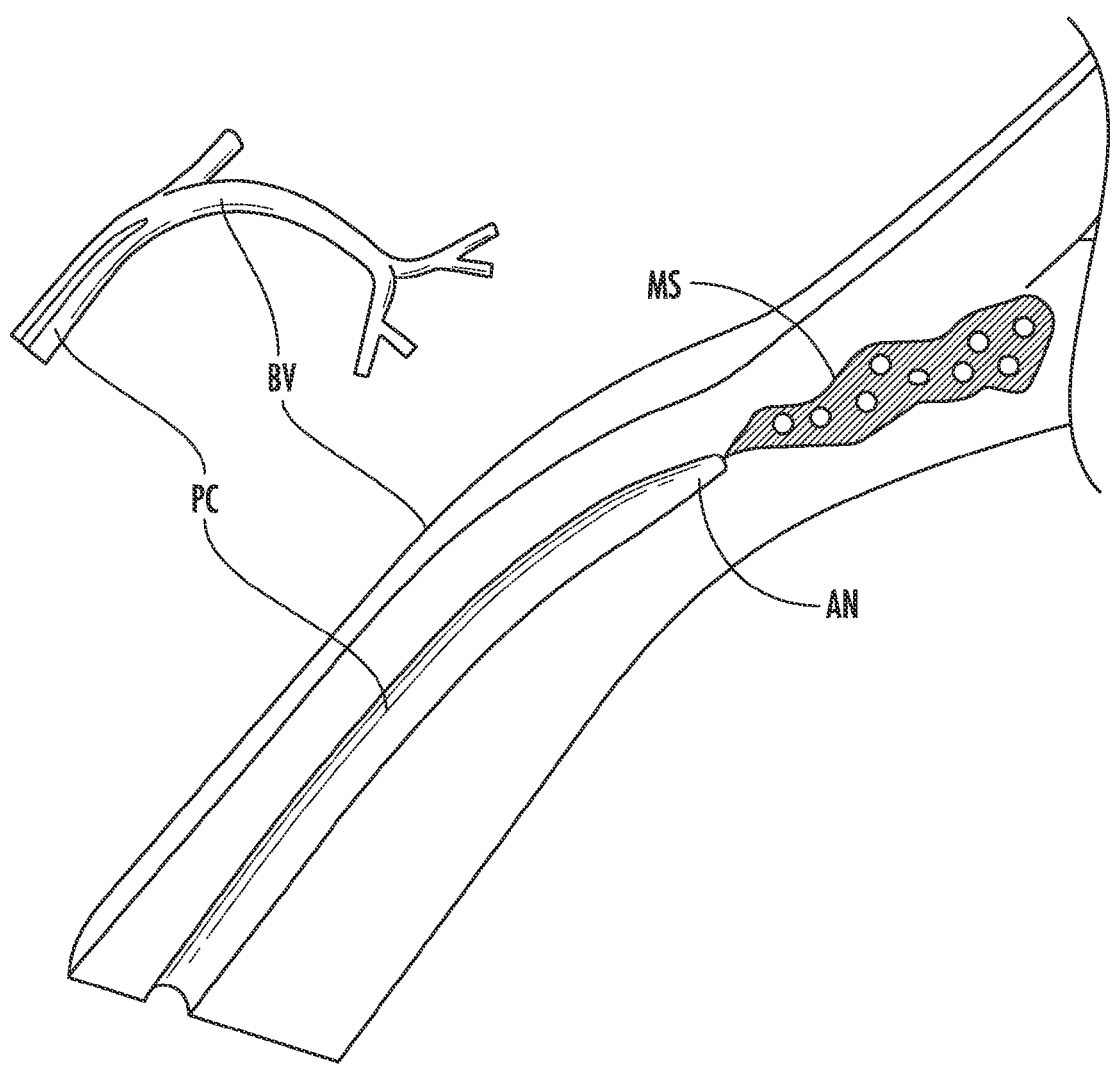
FIG. 11 is a diagram of one embodiment of a catheter (PC) delivering radioactive microspheres (MS) as disclosed herein. The catheter is adjustable axially and radially. AN=adjustable nozzle. BV=blood vessel.

Unlike current drug-delivery catheters, the SMC system provides precise and stable positioning within the vessel cross section and thus allows for desired and even optimal delivery of microspheres and/or drugs within an arterial supply, such as the hepatic arterial supply. Computational fluid-particle dynamic models using patient-specific data determine desired and even optimal axial and radial catheter position for direct tumor targeting. The catheter of the presently disclosed subject matter applies desired and even optimal fluid-particle dynamics theory to radioactive microsphere and/or drug delivery. The catheter can be adjusted in axial and cross-sectional positions enabling desired and even optimal targeting of tumors via specific daughter vessels. Attributes of the SMC include miniaturization, positioning and anchoring, visualization, and surgeon control. See FIG. 11. Referring to FIG. 11, catheter PC, which includes an adjustable nozzle AN, should desirably be positioned in blood vessel BV so as to minimize interference from blood flow, optimize radial position, and securely anchor the tube. Thus, positioning, timing and dosage of the microspheres and/or drugs released are desirably optimized. Inserting the catheter PC causes a disturbance in blood flow. Microspheres MS (and/or drugs, in some embodiments) are released at a suitable moment during the cardiac cycle. There is about a one-fifth of a second window to desirably release microspheres MS. A suitable time to release microspheres MS is at peak systole or during the short period of cardiac cycle deceleration. It is also desirable to optimize the microsphere injection speed in relation to the momentary local blood velocity of the subject. Ideally, as with the SMC positioning, the microsphere-release timing and speed are computationally determined on a patient-specific basis.

Figure 17B:
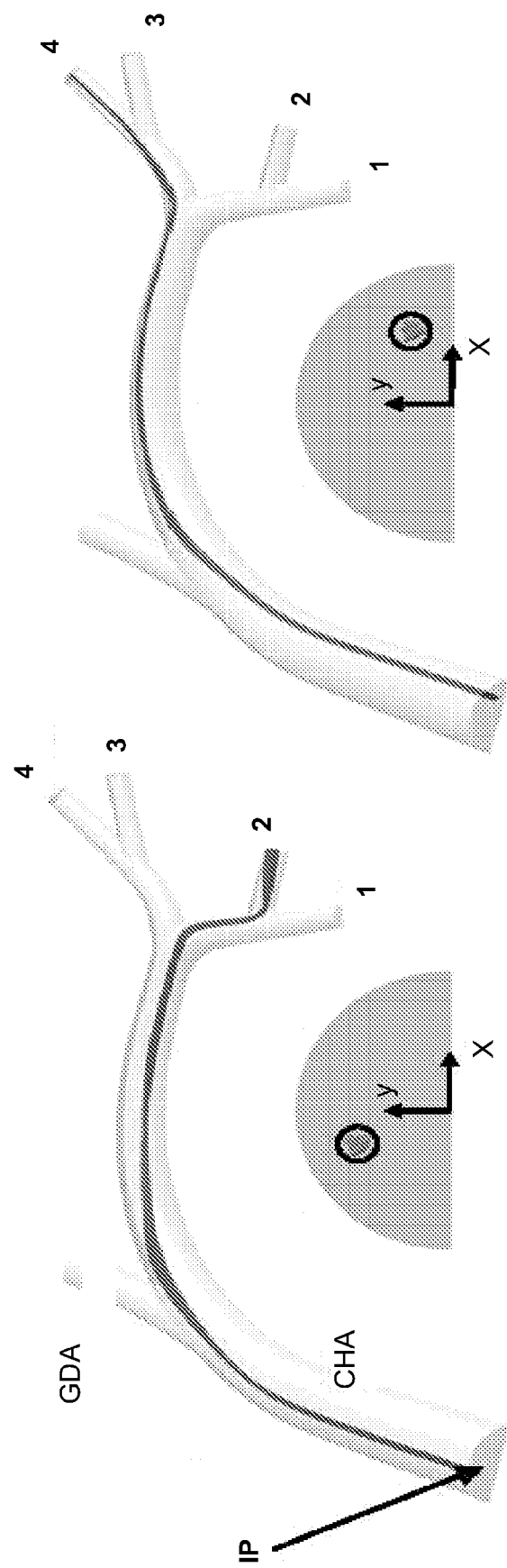

By way of example and not limitation an incorporated microprocessor-controlled syringe pump can ensure, at a desired time interval, suitable delivery volume and infusion speed. Thus, with guidance from computer simulation results, the SMC system can provide controlled, optimally targeted delivery of microspheres (such as radioactive microspheres) and/or drugs directly to a single or multiple tumor sites, the latter after telemetric SMC adjustment following predetermined radial SMC position coordinates. The SMC device and methods described herein provide in some embodiments "direct mechanical targeting" of tumors (FIGS. 17a and 17b).

The SMC is desirably sufficiently small to minimize disturbance in the bloodstream. A desired and ideally optimal position of the SMC is determined by computer simulation. Once the SMC is positioned, it can be anchored, as the release of the particles exerts tiny forces on the catheter. For example, the SMC can be inserted into the body via an incision in the side of the subject. The catheter is inserted through the iliac artery and up the aorta and then into the hepatic artery which branches off of the aorta. See catheter passageway CP in FIGS. 9a-9b. Catheters currently on the market have a flexible tip so that they can be snaked around 90° angles during insertion. However, the only method of positioning is to avoid hitting the arterial wall during insertion. Conventional catheters basically serve as a deployment device. See C in FIG. 9b. There is no radial positioning of the catheter tip. It is fairly routine, for one skilled in the art, to be able to get the catheter in the neighborhood of the target, but optimal targeting and positioning, secure anchoring, and release timing are aspects of the presently disclosed subject matter.

Figure 12:
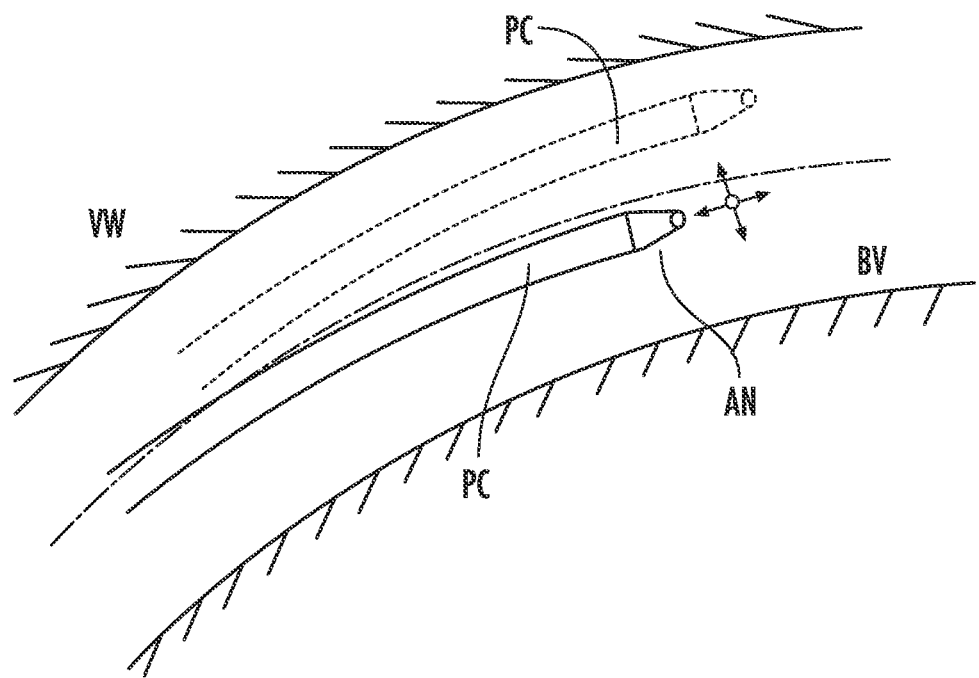
FIG. 12 is a diagram showing adjustable nozzle (AN) in different optimal microsphere release positions in the hepatic artery. The positionable catheter (PC) is shown in two positions, one in dotted and one in straight lines. BV=blood vessel. VW=vessel wall.

The catheter of the presently disclosed subject matter can be controlled in the axial and radial directions. The physician can see the axial position on the display screen via CT scan. See FIG. 12. Referring to FIG. 12, radial and axial positioning of catheter PC within blood vessel BV and/or with respect to vessel wall VW is achieved in manually operated, mechanically operated, and electro-mechanically operated catheter embodiments. In some embodiments robotic catheterization enables precise positioning and anchoring, and hence computer-controlled deployment of microspheres and/or drugs. The unique combination of patient-specific planning and catheter positioning provides unprecedented accuracy in the delivery of therapeutic microspheres and/or drugs.

In some embodiments, an SMC of the presently disclosed subject matter comprises an adjustable nozzle and predetermined placement and orientation for controlled particle release into blood vessels, such as but not limited to the hepatic artery, for the purpose of optimal delivery of an active agent, such as but not limited to therapeutic microspheres (e.g. radioactive microspheres), or other desired micro-drugs. Thus, in some embodiments, the active agent comprises one or more physical characteristics selected from the group including but not limited to: a particle size of from about 1 μM to about 40 μM; a substantially spherical shape; a low density; porous or solid carrying nanodrugs; and with bio-attractive or ferro-magnetic properties. Further, the term "microsphere" can include any particle of micro-scale size or less. Thus, this term can include "nanoparticles"; but, with respect to nanoparticles, tumor-deposition efficiency (which could be 100% for micro-scale particles) could decrease because of (random) Brownian motion effects.

The term "drug" can include any substance used in the diagnoses (such as but not limited to imaging agents, detection agents, and the like), treatment, or prevention of disease or as a component of medication.

Computational analysis provides the subject-specific SMC location. The SMC with a flexible nozzle can be made stationary: (i) via manual CT-scanned adjustment or (ii) via anchoring with "wire-legs," etc. Final matching of the predicted coordinates of the optimal injection point can be achieved via the nozzle angle and nozzle axis adjustments by activating shape-memory alloy wires.

The performance characteristics of the presently disclosed SMC system can be realized in some embodiments through: (1) a combination of sensors; (2) an adaptive SMC device and a reservoir chamber, both of which can be actuated in some embodiments by SMA actuators; and (3) a control logic, which can be based on experimentally validated predictions of a computer simulation model of targeted deposition.

In some embodiments, the presently disclosed SMC system implements a controlled stream, which directs active agents, such as drugs and/or microspheres, to a desired target area with maximum deposition efficiency. The SMC system can work in conjunction with a microsphere and/or drug source and can comprise in some embodiments two components: (i) a microsphere and/or drug injection system, which regulates the pressure/velocity and particle distribution of the microsphere and/or drug source employed; and (ii) a SMC device, having, in some embodiments, control mechanisms for delivering into the bloodstream the embedded particle microsphere and/or drug stream from an optimal release position.

Accordingly, in some embodiments, a combination of a SMC device and a microsphere and/or drug injection system can be used to implement the mechanisms for the control of particle release position.

The presently disclosed subject matter provides in some embodiments a method of delivering an active agent to a target area in the circulatory system of a subject in need thereof. In some embodiments, the method comprises providing a SMC system for directing to a subject a controlled stream comprising an active agent (such as a microsphere and/or drug); and regulating a release position of the controlled stream from the SMC system into the bloodstream to deliver the active agent to a target area of the body of the subject.

The presently disclosed subject matter provides in some particular embodiments a SMC system comprising a microsphere and/or drug source, a microsphere and/or drug injection system and a SMC device, all in flow communication.

The SMC device can comprise a tube having an inlet at one end and an outlet at an opposing end. The targeted drug-microsphere stream release from a computationally predetermined position/segment of the outlet cross-section of the tube, which can be selected based on a desired target area of the body of a subject, can be achieved in some embodiments with an adaptive nozzle positioned within the blood vessel.

In some embodiments, the adaptive nozzle comprises a nozzle tip outlet, which can be deflected by one or more actuators and hence optimally positioned within the blood vessel. In another embodiment, targeted drug-microsphere stream release can be achieved utilizing an adaptive nozzle with variable exit diameters and which is positioned substantially and in some embodiments perfectly parallel to the blood vessel centerline. Determination of targeted release positions from correlated positions on orbits with critical radii allows for constructing the nozzle so as to rotate around a central long axis and arrest on the selected orbits and at orbital locations. Changes in nozzle positioning can be implemented via various mechanisms. Different radial settings can achieve target-specific deposition.

The SMC device can also be equipped with one or more microprocessor sensors to detect the radial position, in relation to the arterial wall, which can be positioned in some embodiments proximal to the tube outlet, such as for example adjacent to the nozzle. Exemplary microprocessor sensors suitable for use with the presently disclosed SMC device include, but are not limited to, silicon micromachined piezoresistive pressure sensing chips, such as those available from Silicon Microstructures, Inc. (Milpitas, Calif., United States Of America). In some embodiments, actuators vary the position of the nozzle to change the alignment of the nozzle outlet.

The sensors can also be electromagnetic sensors that emit a signal as to how far the sensor is from the wall of the artery. This distance can be micrometers or less.

Due to space limitations present in some embodiments of SMC device, it can be desirable in some embodiments to utilize actuators comprising active materials. Exemplary active materials that can be utilized with the presently disclosed subject matter include, but are not limited to, shape memory alloys, shape memory polymers, magnetostrictive materials, and piezoceramic materials.

In some embodiments, the actuators can comprise active materials. Active materials include for example shape memory alloys (SMAs), shape memory polymers, piezoceramic materials, or magnetostrictive materials for actuation and in some embodiments for sensing as well, which allows for the development of highly integrated intelligent systems.

An illustrative example of actuation by active materials is the linear actuation capability of an SMA wire actuator. This material is known to exhibit the highest work output per volume of all known actuation mechanisms, see, e.g. Hollerbach et al. (1992). It can easily be stretched at low temperatures, but upon thermal activation, which can be effected by low-voltage electric power, it contracts, very much like a "metal muscle". Thus, it not only replaces an entire apparatus of gears and other transmission components, but at the same time also provides high actuation force and stroke, is lightweight, and can easily be embedded into structures in a highly flexible way.

Moreover, a prominent SMA, nickel titanium alloy (NiTi), is known for its high biocompatibility, and these attractive features have led to a number of applications in the biomedical field, which range from already well-established applications, like stents and orthodontal braces (Duerig et al., 1999), to more advanced systems like endoscopes actuated by SMA wires (Reynaerts et al., 1999), and micro drug-dosage systems based on SMA thin film pumps (Benard et al., 1998; Makino et al., 2001; Xu et al., 2001). In some embodiments, when shape memory alloys are employed, an alloy of nickel and titanium (NiTi) can be utilized. SMAS can be fabricated as wires, such as for example FLEXINOL® wires produced by Dynalloy, Inc. (Costa Mesa, Calif., UNITED STATES OF AMERICA), and thereby act as SMA actuators. For example, as shown in the particular embodiment illustrated in FIG. 14, a plurality of SMA actuators are operationally linked to an adaptive nozzle near the nozzle inlet and are capable of bracing against the wall of the blood vessel.

The SMC system can increase targeted deposition efficiencies over other micro-catheters known in the art in part through the controlled delivery of the stream comprising an active agent (such as a microsphere and/or drug) into bloodstream through calculated positioning of nozzle tip outlet within the blood vessel. Actuators can be utilized to position the adaptive nozzle, and in particular nozzle tip outlet, to the desired optimum release position for delivery of the microspheres and/or drugs into the bloodstream.

To prevent premature mixing, wall deposition, or particle coagulation, in some embodiments, the adaptive nozzle comprises a flexible material, such as a flexible polymeric material, to permit flexing of the adaptive nozzle by actuators. The nozzle should be flexible enough to enable the necessary deformation and sufficiently stiff to maintain the required shape in the bloodstream. One non-limiting example of a suitable elastomeric material for use in the construction of flexible nozzle includes silicon rubber. It can be desirable to provide in some embodiments surfaces of adaptive nozzle, and in some instances the tube as well, with higher finish tolerances in order to avoid problems with deposition of microsphere and/or drug particles on the arterial wall and turbulence effects.

Manual Operation

Figure 13:
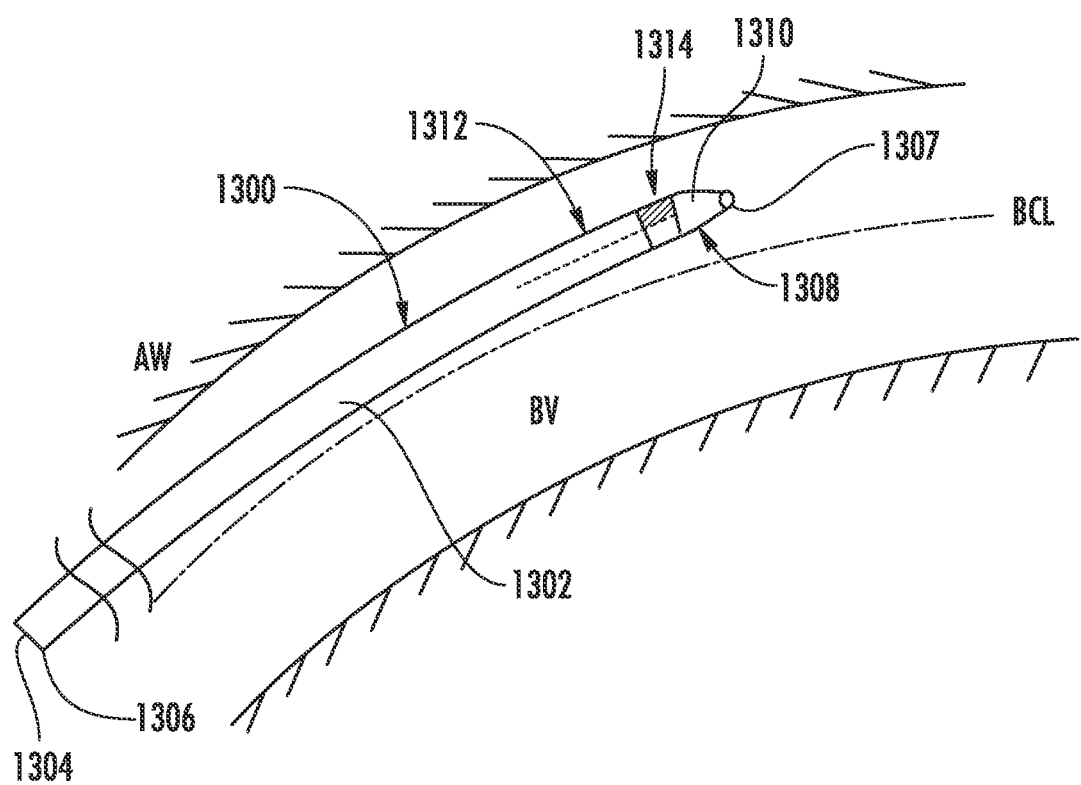
FIG. 13 is a diagram of one embodiment of a manually operated catheter as discussed herein with flexible embedded SMA-rods 1312. A position sensor 1314 near the end 1307 of the nozzle 1308 indicates the catheter's position radially. AW=artery wall. BCL=blood vessel center line (long axis). BV=blood vessel. 1304=inlet. 1306=end. 1310=tip.

Now with reference to FIG. 13, a particular embodiment of a SMC device 1300 is shown. SMC device 1300 comprises a tube 1302 having an inlet 1304 at one end 1306 (show schematically via the broken lines in FIG. 13) and an outlet 1307 with a nozzle 1308 at an opposing end or tip 1310 of SMC device 1300. A microsphere (and/or drug, in some embodiments) stream comprising an active agent is delivered from a microsphere source through adaptive nozzle 1308 into the bloodstream for targeted delivery to a target area of the body of the subject. As shown in FIG. 13, adaptive nozzle 1308 is positioned within the blood vessel BV. Nozzle tip outlet 1307 has a long-axis that is parallel to a long-axis BCL of blood vessel BV.

Continuing with reference to FIG. 13, SMC device 1300 is manually operated. SMC device 1300 comprises a tube 1300, nozzle 1308, and flexible embedded SMA rods 1312 and one or more position sensors 1314. Sensor 1314 is located adjacent to tip 1310 of SMC device 1300 and lets the operator know the radial location of the nozzle tip 1310. Sensor 1314 can be an electromagnetic sensor that sends a signal relative to wall AW of blood vessel BV. On a display screen (not shown) the position of sensor 1314 is compared with the fixed position of where sensor 1314 should be as predicted by the subject specific computer simulation of the optimal release position of the particles. SMC device 1300 is axially positioned using constant CT scans. The doctor manipulates SMC device 1300 very slowly into the position and due to the constant signal from position sensor 1314, knows if it is close or in optimal axial position. SMA-rods 1312 straighten and become rigid. SMC device 1300 is manually manipulated with the aid of sensor feedback regarding the radial position to achieve the desired predetermined position for optimal microsphere release. The released microspheres are carried by the blood to the tumor or other target. Thus, via manual manipulation and with the use of sensor feedback, the desired predetermined positioning is achieved.

The microspheres are suspended in a solution. Using a syringe (not shown), the physician administers the microspheres into a bolus of microsphere-filled fluid and injects them into the SMC tube 1302 at tube inlet 1304 at end 1306.

Mechanical Control

Figure 14:
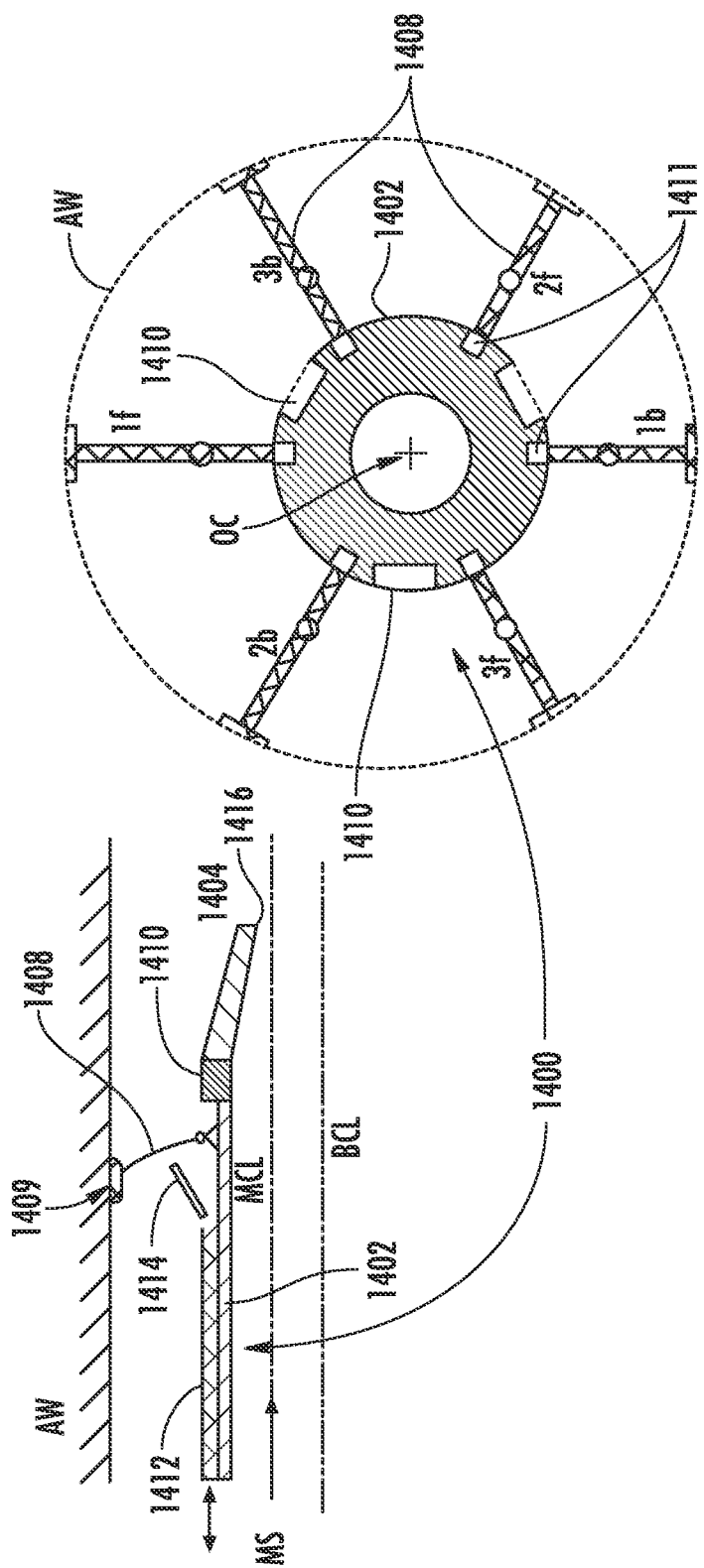
FIG. 14 is a diagram of another embodiment of a mechanically operated catheter 1400 as disclosed herein. A midplane view is on the left and a cross-sectional view is on the right. Shown are six push-rods 1412 which deploy front and back tripod legs 1408, position sensors 1410 and a feedback control loop for employing predetermined positioning. A microprocessor with programmable software allows for patient-specific positioning. The nozzle 1404 tip 1416 is positioned off-center (+) in the exit plane in the right panel of this diagram. AW=arterial wall. MCL=microcatheter center line. BCL=blood vessel center line. MS=$Y^{90}$-microsphere supply. 1400=SMC device. 1402=tube. 1409=tripod shoe (front). 1411=rod/link slots. 1414=link.

In another embodiment, the SMC device is mechanically operated. The SMC device is manually snaked through the blood vessel but is mechanically operated at the positioning phase. With reference now to FIG. 14, SMC device 1400 comprises in some embodiments a tube 1402, nozzle 1404, and push/pull rod(s) 1412 that can deploy tripod legs 1408 to anchor SMC device 1400 in place against wall AW of blood vessel BV. SMC device 1400 can comprise six push-rods 1412 that deploy front and back tripod legs 1408. Position sensors 1410 and a feedback control loop (not shown) assure predetermined positioning. Position sensors 1410 communicate with a microprocessor (not shown) with programmable software that allows for subject-specific positioning and anchoring. Tripod legs 1408 help prevent any movement that might occur from the force of releasing microspheres MS and/or drugs, in some embodiments. Tripod legs 1408 can comprise a bio-compatible material such as titanium. Tripod legs 1408 can comprise tripod shoes 1409 and rod link slots 1411 that are used in the positioning of tube 1402 with respect to vessel (e.g. arterial) wall AW.

One or more SMA actuators (e.g. push rod 1412 and link 1414) can be linked to support tripod legs 1408. When activated, SMA actuators 1412, 1414 can position the support legs 1408 such that nozzle 1404 is aligned or misaligned to varying degrees with blood vessel centerline BCL. By aligning or misaligning nozzle 1404 with blood vessel BV, the release position for microspheres MS flowing into the bloodstream can be controlled depending on the measured and computational fluid-particle dynamics performed during the subject specific simulations. SMC device 1400 is desirably small in size. Tip 1416 of SMC device 1400 is moved parallel to blood vessel centerline BCL in the radial direction for SMC device 1400. Center line MCL of SMC device 1400 moves up and down in a radial direction parallel to vessel center line BCL. The microprocessor provides subject specific positioning. Once SMC device 1400 is anchored, a computer controls the nozzle. See also FIGS. 17a-17b.

Electromechanical Control

Figure 15:
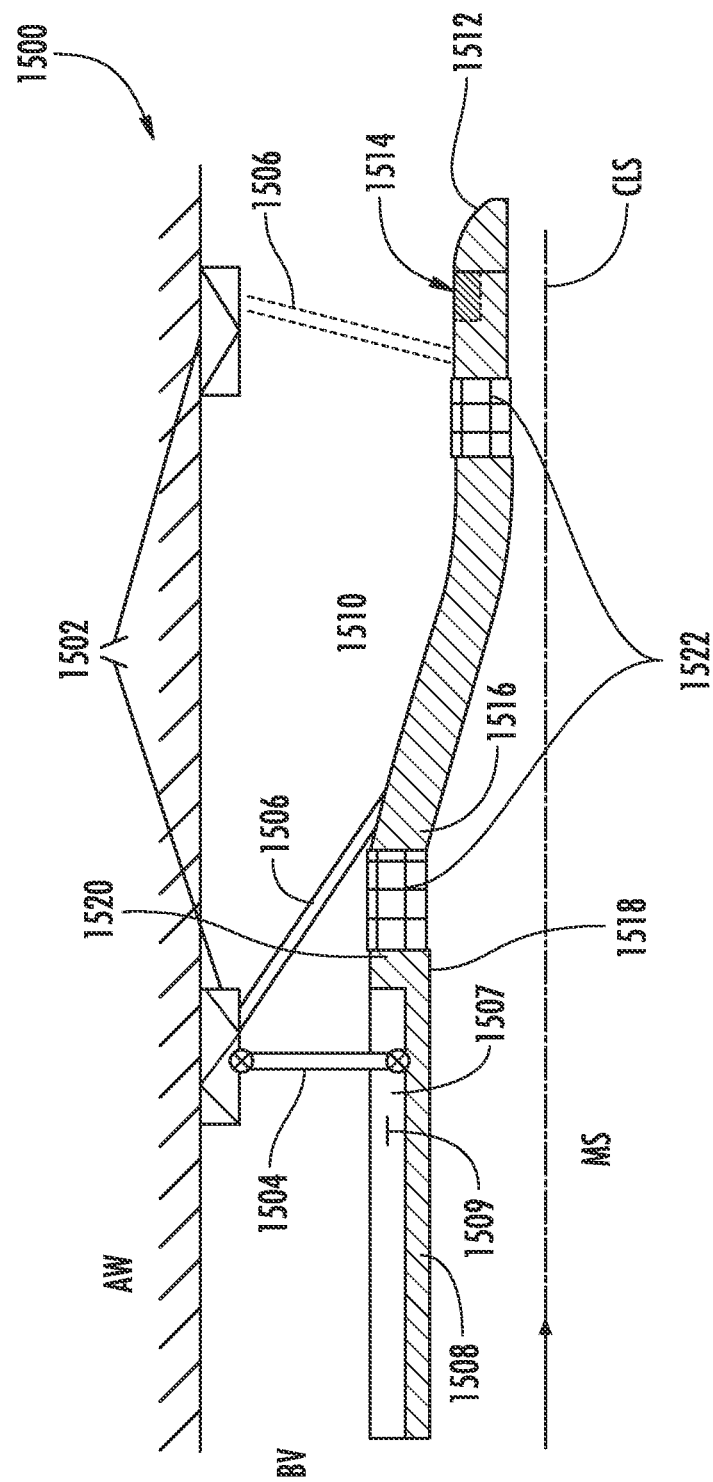
FIG. 15 is a diagram of another embodiment of an electro-mechanical-SMA catheter 1500. Two rubber elements 1522 allow for radial positioning. Support struts 1504 anchor the catheter in place. AW=arterial wall. BV=blood vessel. CLS=center line. MS=$Y^{90}$-microsphere supply. 1502=stent rings. 1506=SMA wires, solid line up, dotted line down. (down). 1507=push/pull rod. 1509=S&S slot with push/pull rod. 1508=SMC front segment. 1510=nozzle. 1512=nozzle tip. 1514=position sensor. 1516=nozzle inlet. 1518=tube outlet. 1520=sealing member.

Referring now to FIG. 15, in yet another embodiment, called electromechanical SMA operation, SMC device 1500 comprises two stent rings 1502 (comprising, for example, NITINOL®/Polymer 2-stage SMM) with adjustable tripod struts 1504 and SMA-wires 1506 are compressed/folded in a slot 1509 in SMC front segment 1508. Struts 1504 and wires 1506 are operably connected to push/pull rod 1507. Once the desired axial position is reached stent rings 1502 are deployed and SMC segment 1508 with nozzle 1510 is centered and anchored via locked-in support struts 1504. In this embodiment centerlines CLS of SMC device 1500 and artery BV are the same. SMA wires 1506 are activated by electric current to position nozzle 1510 plus nozzle tip 1512 according to the predetermined coordinates via a feedback control loop based on position sensor 1514 signals and a subject-specific microprocessor program. After delivery of microspheres MS and/or drugs, in some embodiments, support struts 1504 are unlocked and assist in collapsing stent rings 1502 and SMC device 1500 is removed.

Continuing with reference to FIG. 15, adaptive nozzle 1510 has a nozzle inlet 1516 that sealingly engages tube outlet 1518 and a nozzle tip 1512 that is in axial alignment with centerline CLS of blood vessel BV. This is perpendicularly bisected by tube outlet 1518. Nozzle inlet 1516 can be positioned in flow communication, directly or indirectly, with microsphere source MS. Nozzle tip 1512 is positioned so that the microsphere stream MS is optimally merged with the blood flow. Sealing member 1520 connects nozzle inlet 1516 with tube outlet 1518 to provide a water-tight seal. Sealing member 1520 can be a flexible polymeric O-ring, which can provide both sealing functionality and flexibility to provide mobility to adaptive nozzle 1510 within the blood vessel BV.

Continuing with reference to FIG. 15, in electromechanical SMA operation, center lines CLS of SMC device 1500 and blood vessel BV are the same. In order to get into the radial position, SMC device 1500 has two rubber elements 1522, the first one close to support struts 1504 that work as anchors similar to tripod 1408 of the mechanical operation embodiment (see FIG. 14). SMA wires 1506 can be used to pull the entire front part 1508 of SMC device 1500 and move it away towards wall AW. Second rubber element 1522 is near tip 1512 of SMC device 1500 that pulls it down again, enabling a release of microspheres MS parallel to wall AW at the radial position predicted by the computer simulation. So the majority of SMC device 1500 is centered and anchored with support struts 1504. Front part 1508 of SMC device 1500 is moved and then pulled up into the radial position. At first rubber element 1522 first SMA wire 1506 is deployed, and then second wire 1506 deploys such that nozzle 1510 is parallel to blood vessel wall AW so that radioactive microspheres MS exit nozzle 1510 horizontal or parallel to blood vessel wall AW as desired. The doctor can move nozzle tip 1512 to an axial position of his or her choosing. SMC device 1500 can thus provide a method of attaining the optimal radial position and a method of anchoring itself so that microspheres MS can be released securely. In some embodiments, wherein SMA actuators 1506 operate under tension, an external restoring force can be utilized to return nozzle 1510 to its original position once actuators 1506 are turned off. In some embodiments, the external restoring force is supplied by a spring washer, against which actuators 1506 work.

Figure 19:
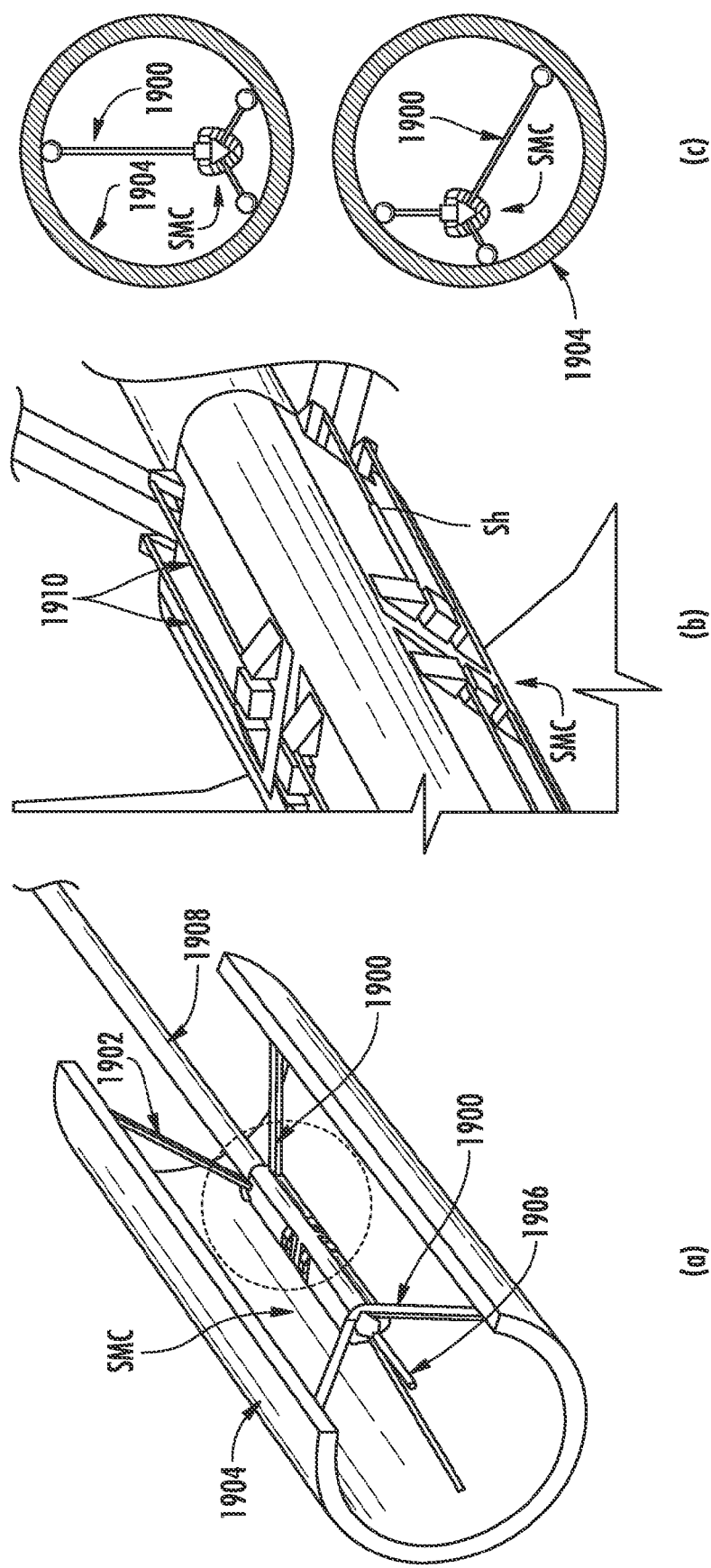
FIGS. 19a-19c are diagrams showing the dual-tripod 1900 design.

In one embodiment, now referring to FIGS. 19a-19c, micro-catheter device SMC features dual tripod supports 1900 to provide and maintain precise control of intra-atrial position and orientation. SMA actuation is used to position catheter legs 1902, which feature antagonistic tendons 1910, for return motion, within blood vessel 1904. Tendons 1910 are made from active materials. SMA tendons 1910 proved sufficient in bandwidth, energy density, and power density for this application. SMC nozzle 1906 and body 1908 are also shown.

A novel robotic catheter, designed for precise control of intra-vessel position, facilitates the accurate delivery of microspheres (e.g. radioactive (e.g. $^{90}$Y) microspheres) and/or drugs as prescribed by simulations. In some embodiments, robotic catheters are tele-operated devices that use SMA tendons to provide high mobility of active bending segments and precise positioning of the catheter tip, two desirable attributes of minimally-invasive surgical technology. In one embodiment, referring to FIG. 20, a model SMC device DC in flow communication with simulated blood vessels is shown. SMC device DC is electromechanically operated in conjunction with a computer-controlled syringe S, specifically designed for targeted microsphere and/or drug deposition. SMC DC is positioned and deployed inside the common hepatic artery CHA. The microspheres and/or drugs are directed to targets located among daughter vessels gastroduodenal artery GDA, proper hepatic artery PHA, left hepatic arteries 3 and 4, and right hepatic arteries 1 and 2. In the model depicted in FIG. 20, a pressure regulation valve PRV and pressure sensor array PSA are also shown. The robotic catheter provides precise arterial positioning at a realistic (1× scale) environment using real-time feedback control. Computational simulations employing representative patient-specific data sets can model the rheology of blood-microsphere/drug dynamics, the presence of the treatment catheter (SMC), the internal microfluidics of the catheter for optimal microsphere and/or drug release, and proper dosage of microsphere and/or drug suspensions from an automated syringe.

In some embodiments a SMC system comprises a SMC device in flow communication with a microsphere and/or drug injection system, which in turn is in flow communication with a microsphere and/or drug source. In some embodiments, the injection system comprises a controllable reservoir chamber. In some embodiments, the controllable reservoir chamber, through a system of microsized pressure sensors and valves allows for the transformation of each microsphere and/or drug source's input into a unified controlled state. The microsphere and/or drug suspension is then directed through adaptive nozzle at nozzle inlet and out through the nozzle tip outlet, where the microsphere and/or drug stream is injected into bloodstream flowing through the blood vessel. For example, in some embodiments a microvalve (e.g., a microvalve available from TiNi Alloy, Inc., San Liandro, Calif., United States of America) can be incorporated into the controllable reservoir. In some embodiments the microvalve uses a thin film SMA actuator.

In some embodiments, an inlet microvalve is placed directly at a reservoir inlet, where it controls entry of the microsphere and/or drug from the microsphere and/or drug source into controllable reservoir chamber. A pressure sensor that measures pressure within controllable reservoir chamber is also placed within active reservoir chamber. Depending on the pressure measured by the sensor, the reservoir chamber can include an outlet microvalve as well that can open an outlet of the active reservoir chamber, which connects with the nozzle inlet, to maintain the level necessary for optimal microsphere injection into bloodstream.

In some embodiments, the microsphere and/or drug release distribution is controlled by keeping the inlet distribution of microspheres uniform (evenly spaced particles). See Example 4. If the inlet distribution of microspheres is uniform a greater percentage is expected to exit into the vessel branch feeding the tumor.

Figure 16:
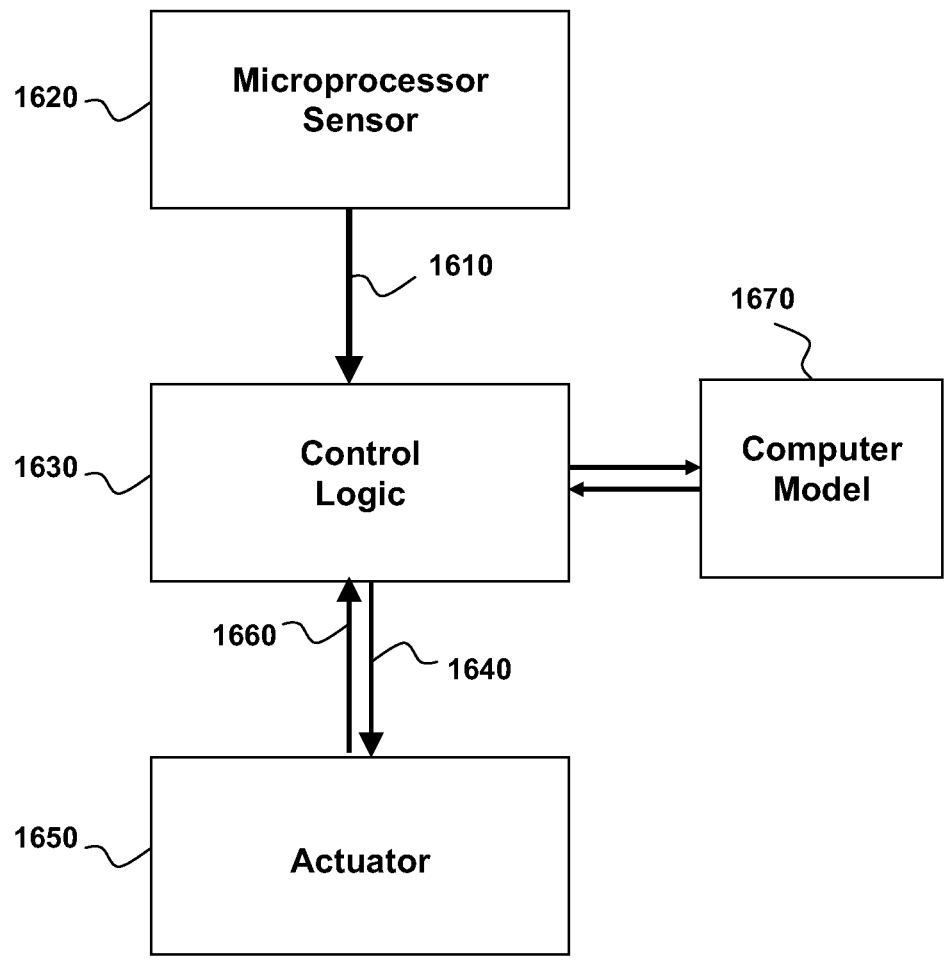
FIG. 16 is a flowchart showing micropressure sensor, control logic, computer model, and actuator interactions.

In some embodiments, the presently disclosed SMC system comprises a control logic that interlinks sensor signals with the corresponding actuator outputs. In some embodiments, for example, as can be seen in FIG. 16, a signal 1610 from one or more microprocessor sensors 1620 is transmitted to a microprocessor comprising a control logic 1630 which interprets signal 1610 and transmits an actuator control signal 1640 to one or more nozzle actuators 1650 which vary the position of the nozzle to change the alignment of the nozzle with the blood vessel, thereby altering the microsphere and/or drug release position. In some embodiments, control logic 1630 responds to signals not only from the microprocessor sensors measuring radial position, but also from signals 1660 originating either from strain gauges or actuators 1650 themselves measuring nozzle positioning. For example, SMA actuators, due to changes in resistivity, can also act as sensors, and therefore these data can be used to determine adaptive nozzle positions before and after actuator changes.

Continuing with FIG. 16, the control logic algorithm can be in operational communication with a computer model 1670 for fluid particle flow, which provides computational fluid-particle dynamics results that determine the desired position of adaptive nozzle and therefore prescribes the desired actuator set points to direct the active agent to the target area of the body of the subject. In some embodiments, the control approach is based on a standard proportional-integral-derivative (PID) algorithm. One of ordinary skill in the art would recognize that other algorithms can be suitable for use with the presently disclosed subject matter, upon a review of the same.

Unlike other forms of brachytherapy where placement of radioactive sources is controlled manually, intra-arterial radiation therapy is comparatively uncontrolled by the operator. Although it has been reported that in properly treated subjects the majority of microspheres do collect in tumor vasculature additional safety, lower toxicity and likely greater anti-tumor outcomes are realized with improved accuracy of microsphere and/or drug deposition. There is a sizeable amount of literature on the use of $^{90}$Y microspheres dating back to the early 1950's, and there are currently large worldwide clinical trials enrolling hundreds of subjects each. Hence, the fundamentals of the technique are well known regarding the current state-of-the-art in the delivery of both resin and glass $^{90}$Y microspheres. However, before the development of the presently disclosed subject matter, there has not been a way to preplan the implant as is done with traditional radiation sources, nor has there been an accurate way of determining a post-plan summary of radiation dose. Use of a robust computer modeling solution in accordance with the presently disclosed subject matter can enable treatment teams to predict where and in what concentration microspheres will deposit, and thus preplan an individual treatment. Secondly, post-treatment radiation dosimetry can be developed with input of the treatment parameters.

This presently disclosed subject matter demonstrates that computer simulations of blood flow and microparticle transport applied to a representative artery system elucidates new physical insight. For example, bifurcating vessel geometry, type of particle inlet distribution and pressure boundary conditions are major factors influencing targeted delivery of microspheres into tumors. This has a direct effect on the total activity delivered and ultimately total absorbed dose of radiation in the tumor and normal tissues. Therefore, computational fluid-particle dynamics (CF-PD) techniques provide realistic, accurate and cost-effective tools for the analysis of blood flow and particle transport in arterial systems, with the overall goal of optimal targeted delivery of microspheres to predetermined sites.

Computer simulations of both blood flow patterns and microsphere and/or drug dynamics provide valuable insight on how to optimize microsphere and/or drug implantation into patho-physiologic areas (e.g. tumors) while sparing normal tissue. Computational analyses of microsphere and/or drug transport in blood flow for subject-specific cases provides information needed to optimize microsphere and/or drug characteristics as well as the procedure of implantation into hepatic tumors or other patho-physiological targets, while sparing normal tissues.

Experimentally validated computer simulation results demonstrate that the anatomic morphology of an arterial system, such as but not limited to hepatic arterial system, and corresponding downstream resistance to blood flow are aspects in determining global and local blood flow distribution. Furthermore, the type of microparticle release distribution and/or the release position has a significant impact on particle trajectories and ultimately on targeted delivery to a predetermined site. The observation of parabolic particle injection concentration, in conjunction with a parabolic inlet velocity profile, yielding local particle exit percentages similar to the local flow distributions demonstrates that equivalent upstream particle and velocity profiles can have particle-mass outflow distributions similar to the carrier fluid.

Desirable SMC positioning employs subject-specific computer simulations of the relevant particle-hemodynamics plus the physical implementation as described herein. Petascale computing allows for realistic, fast, and cost-effective data results; furthermore, available SMCs can be modified to have the adjustable nozzle and SMC anchoring and orientation of the presently disclosed subject matter.

Electromagnetic sensing (3D Guidance trakSTAR™, Ascension Technology Corporation, Burlington, Vt., United States of America) of catheter position (X,Y,Z) and orientation (roll, pitch, yaw) can result in desired catheter placement to within 0.5 mm. Computer-controlled delivery of the microsphere and/or drug suspension is achieved using an automated syringe pump.

Thus, disclosed herein are methods, devices, and systems for providing controlled streams of active agent (such as microsphere and/or drug streams) where most of the active agent (e.g. drug microspheres) reach the desired target area based on simulations relying on computational fluid-particle dynamics (CFPD) techniques. The methods and systems were successfully tested for microparticle targeting on a tumor fed by four daughter vessels within the hepatic artery. A validated computer simulation model included consideration of optimal particle characteristics and release position. Further testing and validation in physical models utilizing embodiments of the SMC system are disclosed in the Examples following.

EXAMPLES

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

The present study employed an experimentally validated patient-specific computer simulation model for hepatic blood flow and $^{90}$Y-microsphere and/or drug transport to determine the influence that multiple factors have on particle injection and transport leading to controlled radiation dose delivery. An overall goal was to facilitate optimal targeting of more radiation to patient-specific tumors, and also to discover how to achieve greater safety and protection of the liver and the upper gastrointestinal tract from unintended microsphere and/or drug deposition.

No previous data was known regarding the impact of local blood flow dynamics on $^{90}$Y-microsphere transport and distribution in the human hepatic arterial system.

In brief, a suitable physical replica of the hepatic artery portion of a human circulatory system was designed and built, and then the SMC's ability to target specific regions of the body for particle deposition was quantitatively measured. Although there is variability in exact blood vessel morphology from person to person (based on gender, age, size, etc.) the models built can be representative of a typical hepatic artery morphology. An advantage of a tightly coupled computational/experimental approach is that controlled and reproducible experiments are used to validate the computational models. The computational models are then used in further assessments to explore the effects of blood vessel morphology variations on particle trajectories and deposition, together with clinical testing.

The blood vessel replica and SMC components were combined to show that individual branches of the simplified blood vessel replica were targeted. A computer prediction model was used to determine the microsphere release position and inlet flow conditions, the nozzle system was used to adjust to the predicted position, and a laser detection system measures microsphere concentration in each of the individual outlets to verify the ability to target individual branches in agreement with the model predictions.

The local deposition efficiency was also validated. To this end, the focus can be on one particular branch of the system, in which an artificial tumor of varying size is placed. The microsphere deposition on the artificial tumor was then predicted and measured.

The model used in the examples below assumed steady blood flow, rigid vessel walls, non-interacting particles, fixed microsphere physical characteristics, zero relative particle Reynolds number, and singular particle injection location will be lifted in future works. Additionally, the vascular geometry was idealized through one symmetric representation of a wide array of hepatic artery morphologies.

Example 1

Computer Modeling, Generally

A three-dimensional (3-D) computer model was developed to analyze and simulate blood-microsphere flow dynamics in the hepatic arterial system with a tumor. Supplemental geometric and flow data sets from subjects undergoing RE were used to validate the accuracy of the computer simulation model. Specifically, vessel diameters, curvatures and branching patterns, as well as blood flow velocities/pressures and microsphere characteristics, i.e., diameter and specific gravity, were measured. 3-D computer-aided design software was used to create the vessel geometries. Initial trials, with 10,000 non-interacting microspheres released into the hepatic artery, used resin spheres of 32-micron diameter with a density twice that of blood.

Example 2

Modeling Procedure

Figure 1:
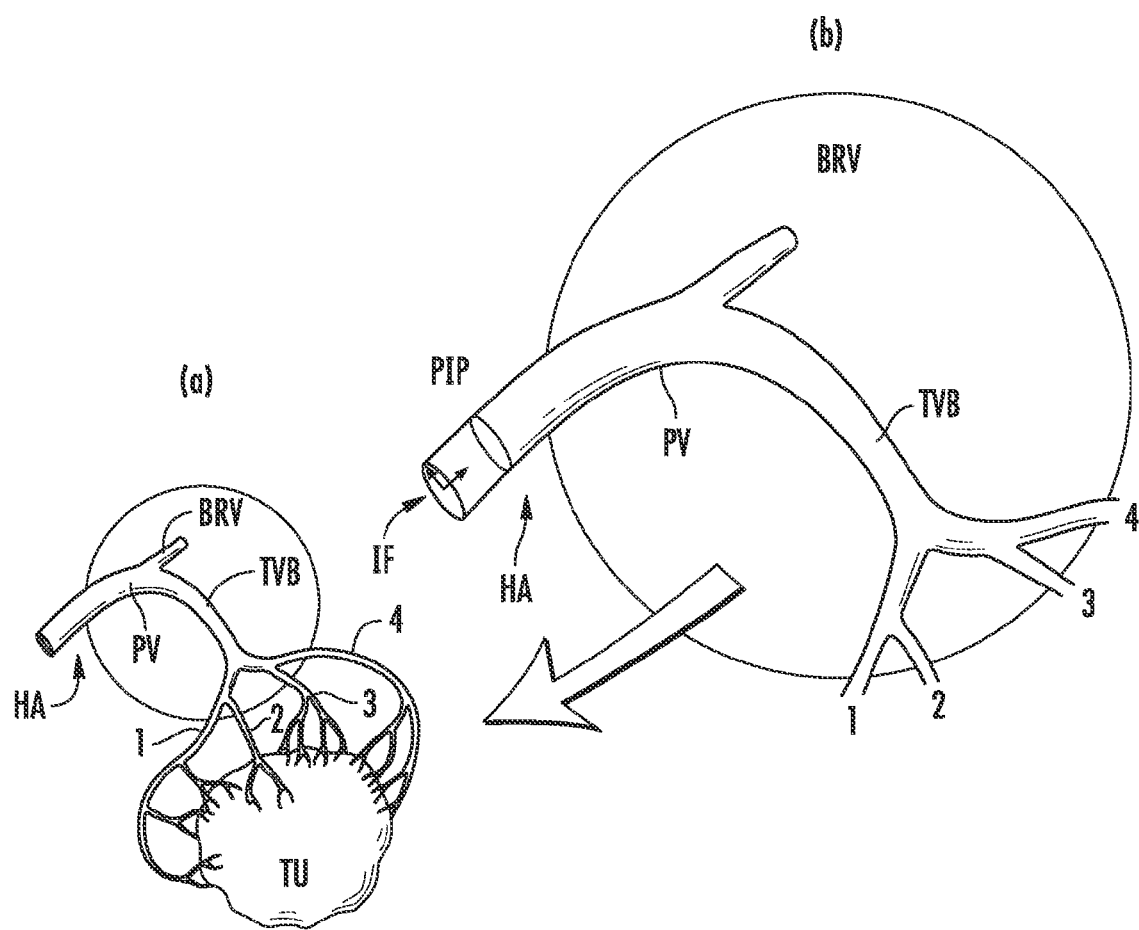
FIGS. 1a-1b are schematic diagrams showing the hepatic arterial (HA) system geometry.

Based on previously published fluid-particle dynamics results, a 3-D computer model was developed to analyze and simulate blood-microsphere flow dynamics in a rigid hepatic arterial system with branching vessels leading to a tumor (see FIGS. 1a, 1b). Specifically, vessel diameters, curvatures and branching patterns, as well as blood flow velocities/pressures and microsphere characteristics, i.e., diameter and specific gravity, were selected based on representative biological data. SOLIDWORKS® 3-D computer-aided design (CAD) software was used to create the vessel geometries. It included a curved right hepatic artery HA with one branch vessel BRV to the normal liver and a tumor vessel branch TVB leading to a quadruple-branch daughter vessel 1, 2, 3, 4 leading selectively to a tumor TU. All bifurcations were in-plane and cross-sectional areas were modeled as circular regions, which enabled the domain to have a symmetric boundary, leading to a 50% reduction of the computational domain (FIGS. 1a and 1b). Boundary conditions included no-slip wall velocity, parabolic inlet velocity profile, and uniform outlet pressures. Blood flow and particle transport were described by the conservation principles of mass and momentum and Newton's second law of motion, respectively. A non-Newtonian blood viscosity model was employed with restitution coefficient of 1.0 on all walls (i.e. no particle deposition along the vessel wall possible). Presently steady flow was assumed with a Reynolds number of 1150, which is calculated as an effective Reynolds to approximate normal pulsatile blood flow.

Particle dynamics modeling assumed one-way coupling and relied on the drag force being dominant neglecting possible gravitational effects. Two particle-injection distributions (i.e., uniform and parabolic) at the inlet particle injection plane PIP of the main hepatic artery HA were considered, where the particle injection velocity matched the local blood velocity. Particle-release-position maps, showing the departure points of individual particles reaching specific arterial outlets, were generated based on a "backtracking" method discussed by Kleinstreuer. Initial trials, with 10,000 non-interacting microspheres released into the hepatic artery HA at inflow IF, utilized resin microspheres of 32 micron diameter with a density twice that of blood. The particle suspension was dilute, i.e., non-interacting microspheres, due to the very low particle volume fraction.

Example 3

Particle Trajectory Validation

Figure 2A:
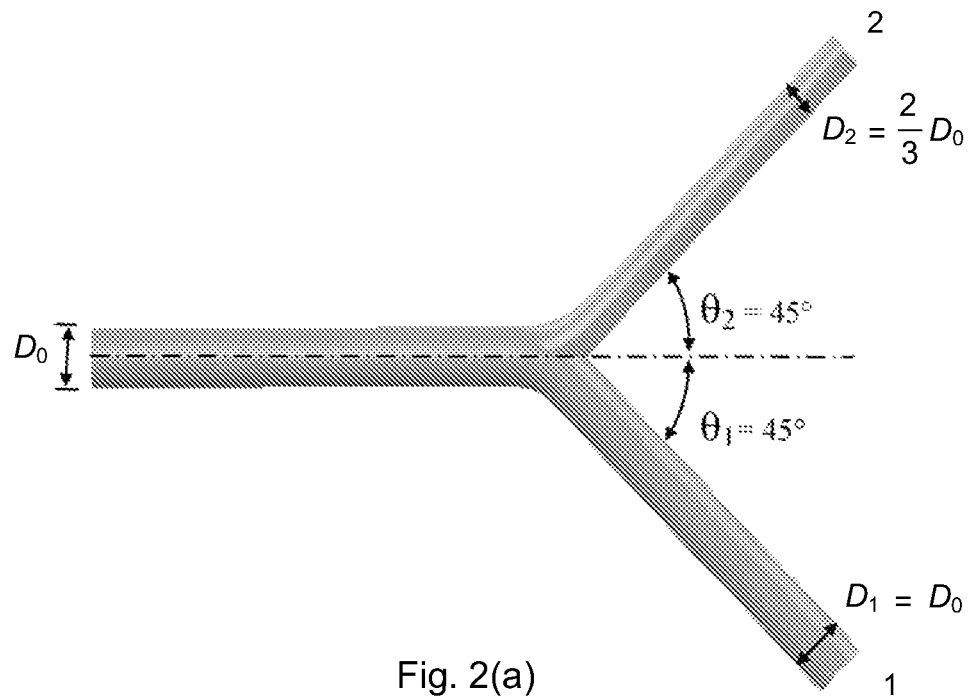
FIGS. 2a-2b are a schematic diagram and graph, respectively, based on the system of FIGS. 1a and 1b and show computer model validation.
Figure 2B:
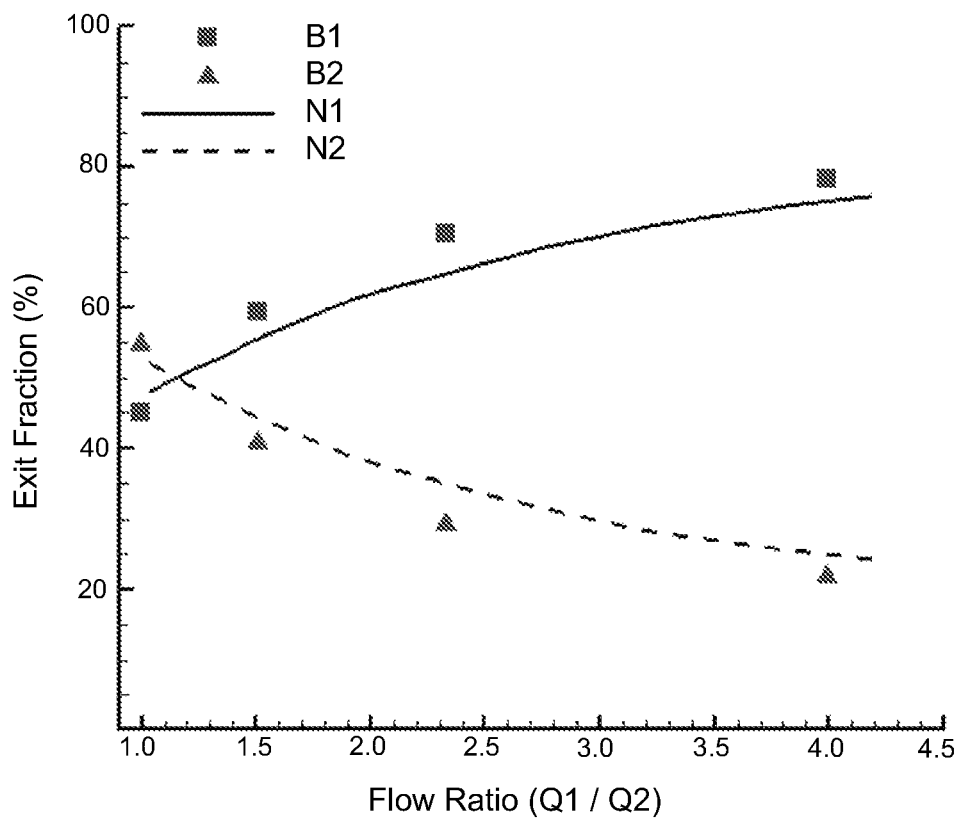

The accuracy of the computer simulations using the commercial software CFX (Ansys, Inc., Canonsburg, Pa., United States of America) to model micron particle behavior has been validated in terms of particle deposition in human airways. In addition, to demonstrate accurate particle tracking, computational simulation results have been compared to experiments with a single bifurcation conducted by Bushi (Bushi et al. 2005). Steady flow corresponding to an inlet Reynolds number of 500 carried neutrally buoyant particles of 0.6 mm in diameter through the domain. The walls of the domain did not allow any particle deposition and the daughter branches 1, 2, 3, 4 (FIGS. 1a and 1b) of the bifurcation had different diameters. FIGS. 2a and 2b illustrate the single bifurcation geometry along with the good matching between the experimentally recorded and the computationally predicted behavior of particles exiting the domain under different flow rates through each daughter branch of the bifurcation. Thus, the present computer model is a reliable simulation tool to predict and analyze blood-microsphere dynamics in branching vessels.

Example 4

Varying Inlet Distribution and Outlet Pressure Conditions

Computational simulations of particle transport within a carrier fluid have the potential to accurately reproduce experimental observations and trends of particle trajectories and deposition patterns. The present study focused on blood flow and micron-scale particle transport and injection distribution within a representative hepatic artery system (see FIGS. 1a-2b for geometric data).

Simulations of blood flow subject to different branch-outlet pressures as well as blood-microsphere transport were successfully carried out. The simulations allowed for testing of two types of microsphere release distributions in inlet plane PIP of the main hepatic artery HA. If the inlet distribution of microspheres was uniform (evenly spaced particles) a greater percentage would exit into the vessel branch TVB feeding tumor TU (See FIGS. 1a and 1b). Conversely, a parabolic inlet distribution of microspheres (more particles around the vessel center) showed a high percentage of microspheres exiting branch vessel BRV leading to the normal liver.

Example 5

Blood Flow

Figure 3A:
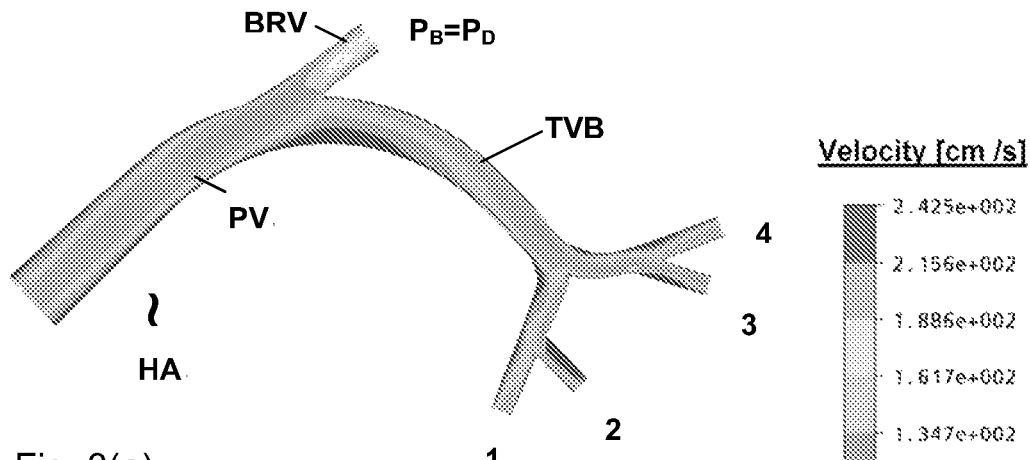
FIGS. 3a-3b are schematic diagrams based on the hepatic arterial (HA) system of FIGS. 1a and 1b and show blood velocity fields for two scenarios having different branch-outlet (1, 2, 3, 4) pressures.
Figure 3B:
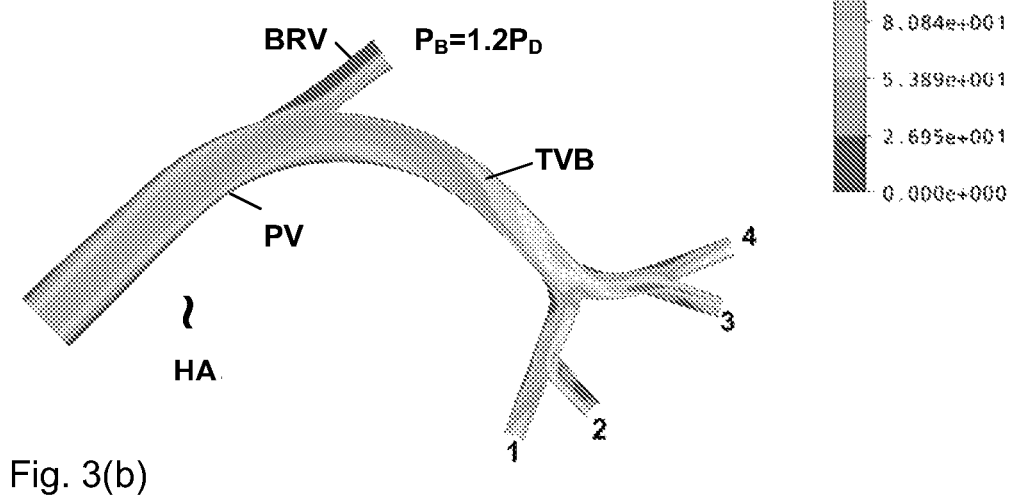

The effect of downstream resistances in a major hepatic artery branch, in terms of varying outlet pressures $P_D$, on the blood supply via four daughter vessels connected to a tumor was assessed (see FIGS. 3a-4b). FIGS. 3a and 3b depict the velocity fields when the branch-outlet pressure is equal to (or 20% higher than) the outlet pressures of the four daughter vessels 1, 2, 3, 4. In the second case, say, due to a natural or induced elevated resistance in the branch, more blood flows towards the tumor (not shown in FIGS. 3a-3b) with a slight preference for daughter vessel 3. In fact, about 80% of the volumetric flow rate (Q) is conveyed towards the tumor via the four daughter vessels 1, 2, 3, 4, up from 42% when all the outlet pressures were the same (see FIG. 3a). Of special interest are the flow rate distributions exiting daughter branches 1, 2, 3, 4 in light of the two pressure boundary conditions upstream. As can be deduced from FIGS. 3a-3b, daughter vessel 3 receives most of the flow (approximately 28%); however, in all cases the changing branch-outlet pressure has no discernable effect on the local flow rate distribution, i.e., $\Delta Q|_{max} \approx 2\%$ (see FIG. 3b). The flow distributions in daughter branches 1, 2, 3, 4 result from the unique interplay of the present vessel geometry and related flow structures. An increase in branch vessel pressure results in increased flow to the daughter vessels, but does not alter the daughter vessel's relative flow rates because the outlet pressures of the daughter vessels remain the same.

Example 6

Particle Transport

Ideally, all injected $^{90}$Y-microspheres should reach, via the blood-supply vessels, the periphery of the tumor. Many variables are associated with that goal, which can be subject-specific. The variables can include vessel geometry, particle characteristics, injection point, particle release distribution, and local blood flow structures. For the present idealized study, 10,000 32-μm particles were uniformly and parabolically distributed in inlet plane PIP of the main hepatic artery HA (see FIG. 1b and FIGS. 5a, 5b). As previously stated, the microspheres do not actually interfere with each other; although, in FIGS. 5a, 5b and 7 it appears graphically that they touch or even overlap. Of interest are the percent quantities of particles exiting four daughter vessels 1, 2, 3, 4 toward the tumor under different inlet and pressure boundary conditions. For example, FIG. 6 shows the particle exit percentages for the two inlet distributions subject to equal outlet pressure for all branches. The "global exit-percentage" is defined as the number of particles exiting a specific vessel divided by the total number of particles injected upstream. Referring to FIGS. 1a and 1b, the geometric alignment of the hepatic branch BRV with the main artery HA, a parabolic particle inlet distribution conveys most of the microspheres through branch vessel BRV (58%) and the rest almost evenly distributed among the four daughter vessels 1, 2, 3, 4 flowing towards tumor TU. The scenario is quite the opposite when switching to a uniform particle injection, where daughter outlets 2 and 3 each deliver about 20% of the microspheres and outlets 1 and 4 nearly 10% each.

Figure 4A:
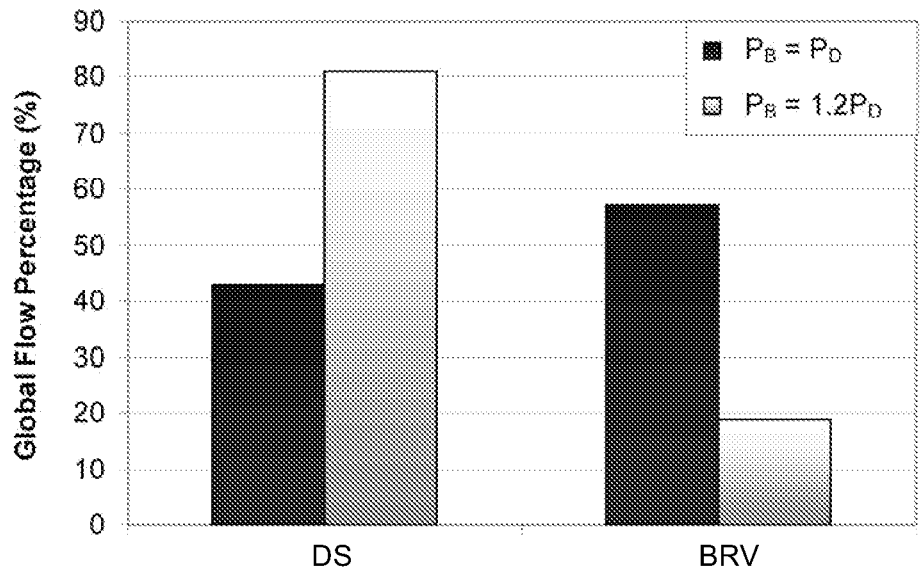
FIGS. 4a-4b are graphs showing varying exit flow rate distributions in daughter vessels and the hepatic branch (BRV) presented in FIGS. 1a and 1b for different pressure levels.
Figure 4B:
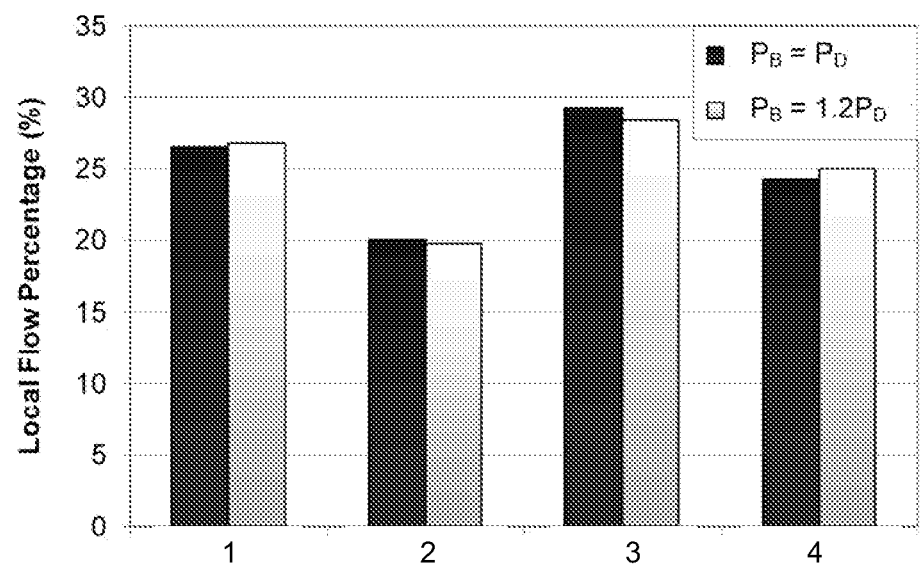
Figure 8:
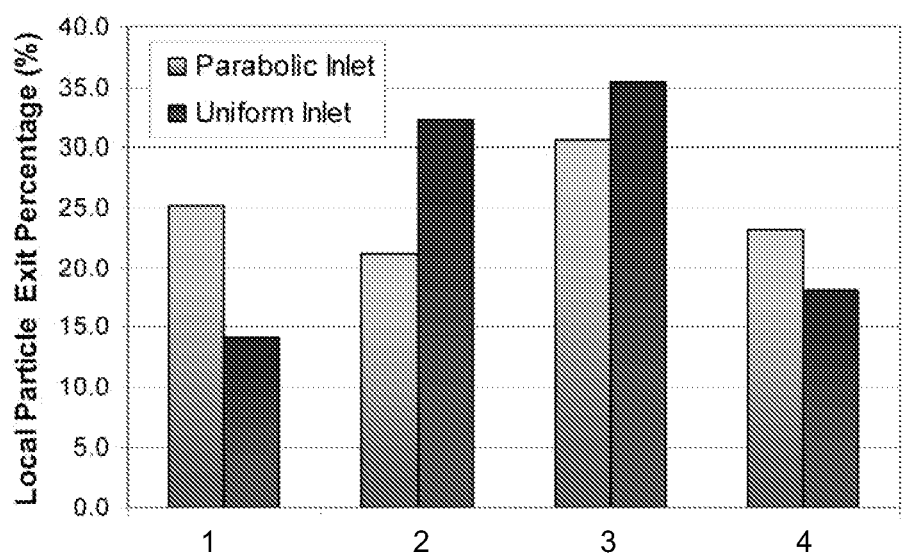
FIG. 8 is a graph showing daughter vessel (FIGS. 1a-1b) exit distributions in terms of local particle percentages resulting from uniform (dark bars) and parabolic (lighter bars) inlet distributions. "Local particle exit-percentage" is the number of particles exiting a specific daughter vessel divided by the total number of particles exiting all four outlets.

An additional variable influencing the amount of particles exiting specific daughter vessels is the branch-outlet pressure. The "local exit-percentage" is defined as number of particles exiting a specific daughter vessel divided by the total number of particles exiting all four outlets. FIGS. 4b and 8 depict both local flow rate distributions and particle percentages among the four daughter vessels 1, 2, 3, 4 subject to different branch-outlet pressures and particle inlet profiles, respectively. While the two branch-outlet pressures have no effect on the individual local flow rates in the daughter vessels 1, 2, 3, 4 (FIG. 4b), the type of particle inlet profile measurably affects the exiting Y-particle quantity in each daughter vessel (FIG. 8). Clearly, particle inertia effects causing streamline crossing, convey (for a uniform release) 58% of the injected microspheres to the daughter branches where vessels 2 and 3 (see FIGS. 1a and 1b) receive the majority of the microspheres (see FIGS. 6 and 8). As a result, the relative particle concentrations (FIG. 8) do not follow the relative (i.e., local) flow rates in the daughter vessels 1, 2, 3, 4 (see FIG. 4b). In contrast, for a parabolic particle release, the exiting particle concentrations (FIG. 8) are almost proportional to the relative (i.e., local) flow rates in the daughter vessels 1, 2, 3, 4 (FIG. 4b). The observation that a parabolic particle injection concentration, in conjunction with a parabolic inlet velocity profile, yields local particle exit percentages very similar to the local flow distributions suggests that equivalent upstream particle and velocity profiles may have similar outflow distributions for both particle-mass and blood volumetric flow rate.

Example 7

Experimental Validation of Targeted Microparticle Delivery

Figure 20:
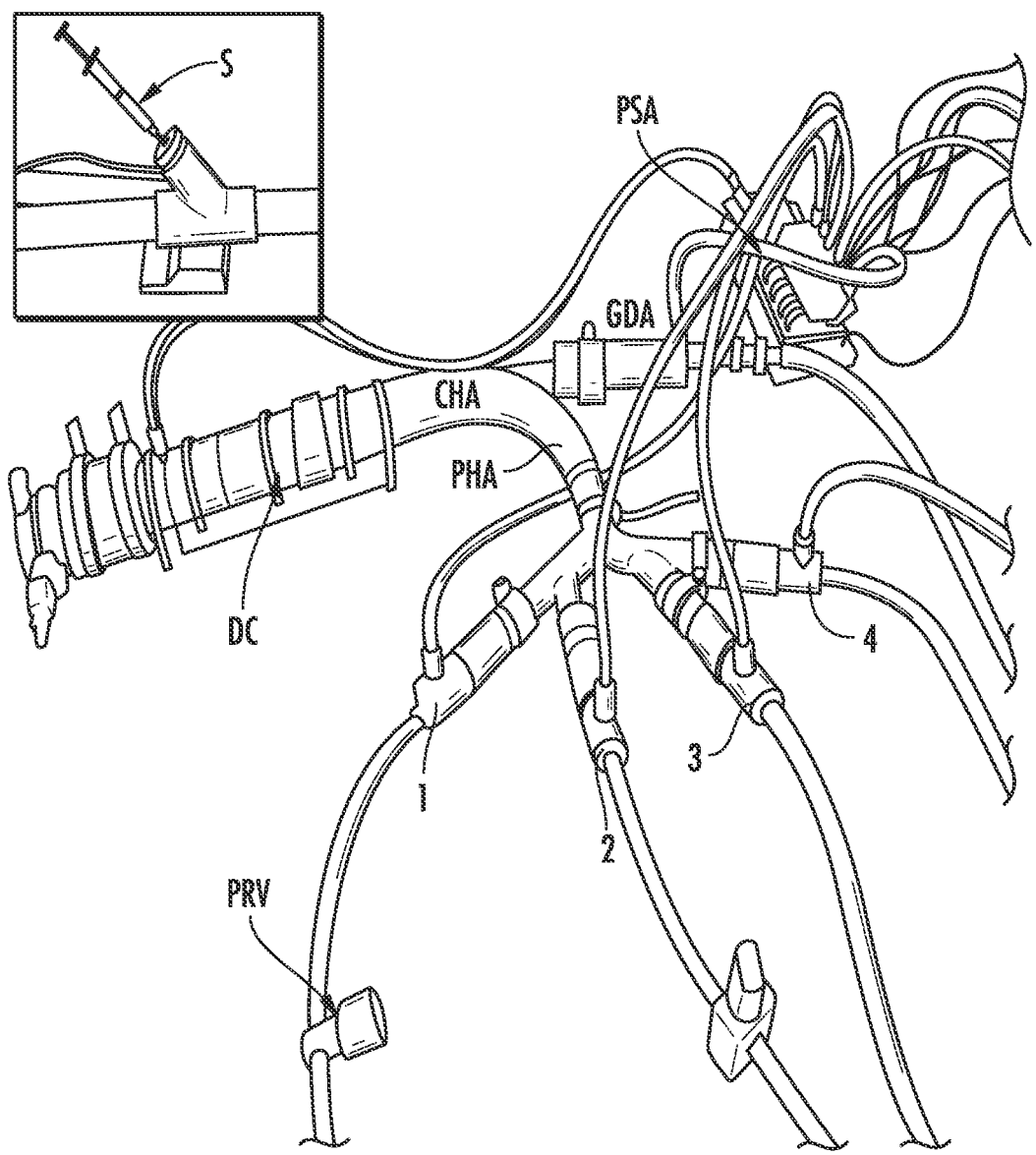
FIG. 20 is a drawing of a 4×-scale experimental setup showing the hepatic artery model and active agent deployment syringe (S) (inset). CHA=common hepatic artery, DC=deployment catheter, GDA=gastroduodenal artery, PHA=proper hepatic artery, PRV=pressure regulation valve, PSA=pressure sensor array. Daughter vessels 1 and 2 are right hepatic arteries. Daughter vessels 3 and 4 are left hepatic arteries.

A CF-PD model of the human hepatic arterial system was developed and experiments were validated using a scaled model. The 4× scale hepatic artery model (major vessel branching into 1 major and 4 minor daughter vessels) was designed based on data from human hepatic arterial anatomy and fabricated in a transparent high-impact resin using 3D rapid prototyping technologies (FIG. 20). The hepatic artery model was incorporated into a closed fluids system that provided steady, laminar flow with pressure and volumetric flow rate scaled to match human hemodynamics.

Figure 21A:
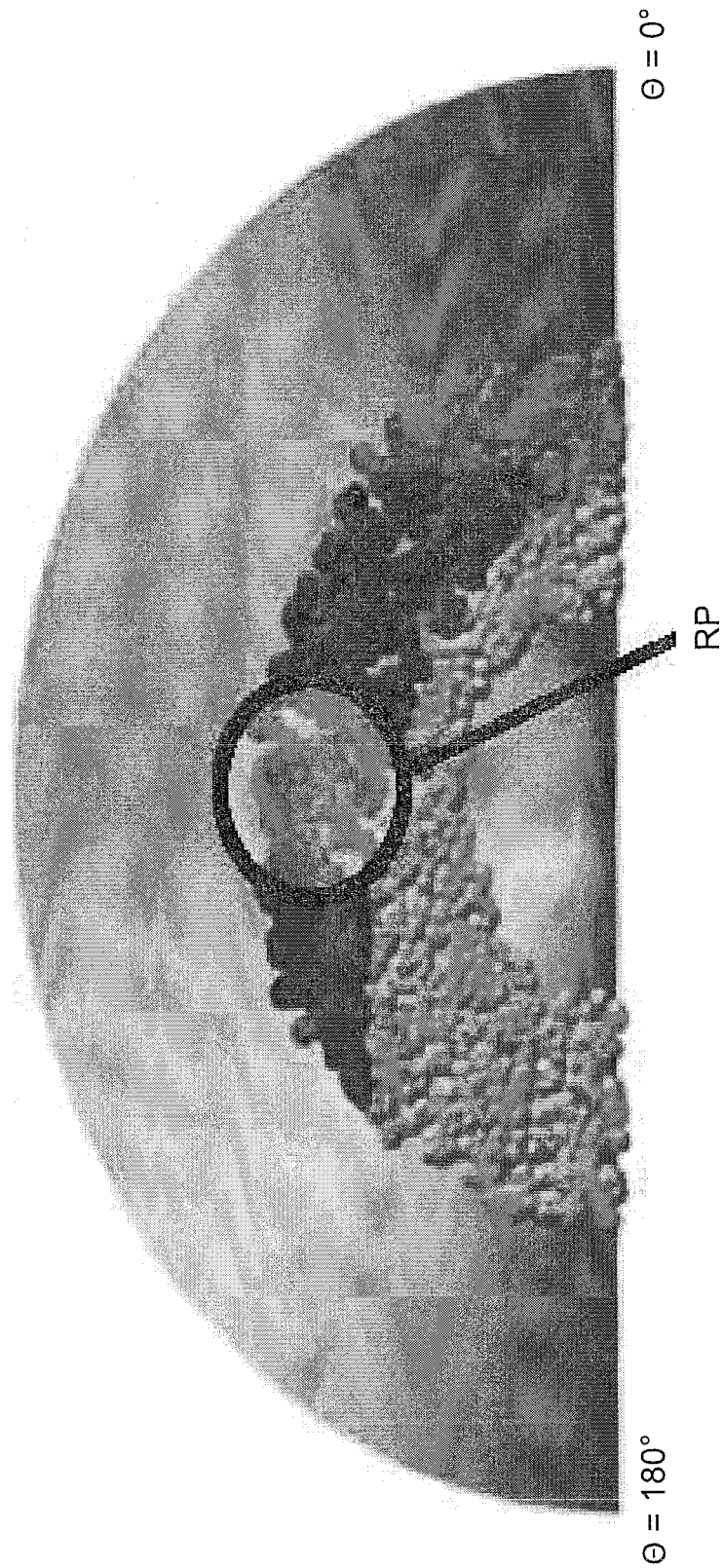
FIGS. 21a-21d show a diagram, photograph, and graphs of computer-guided experimental results illustrating preferential particle exit locations.
Figure 21B:
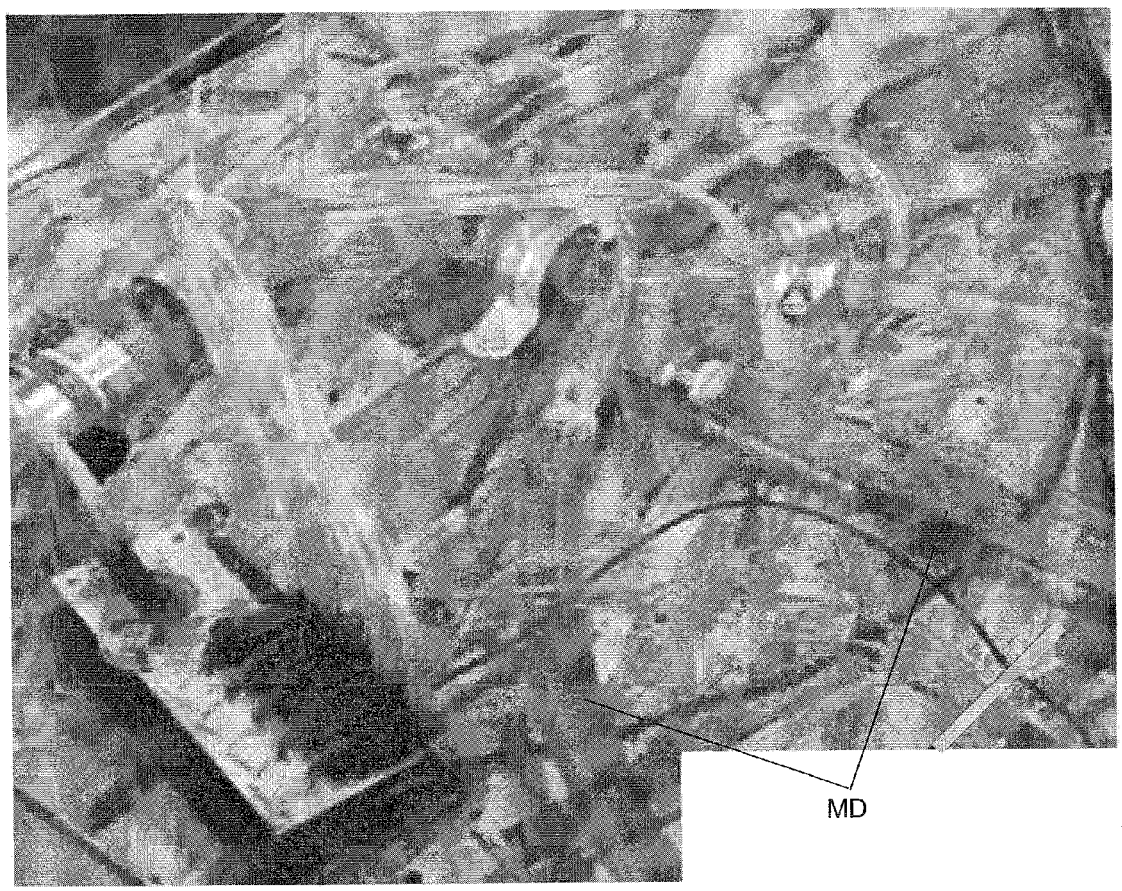
Figure 21C:
Figure 21D:
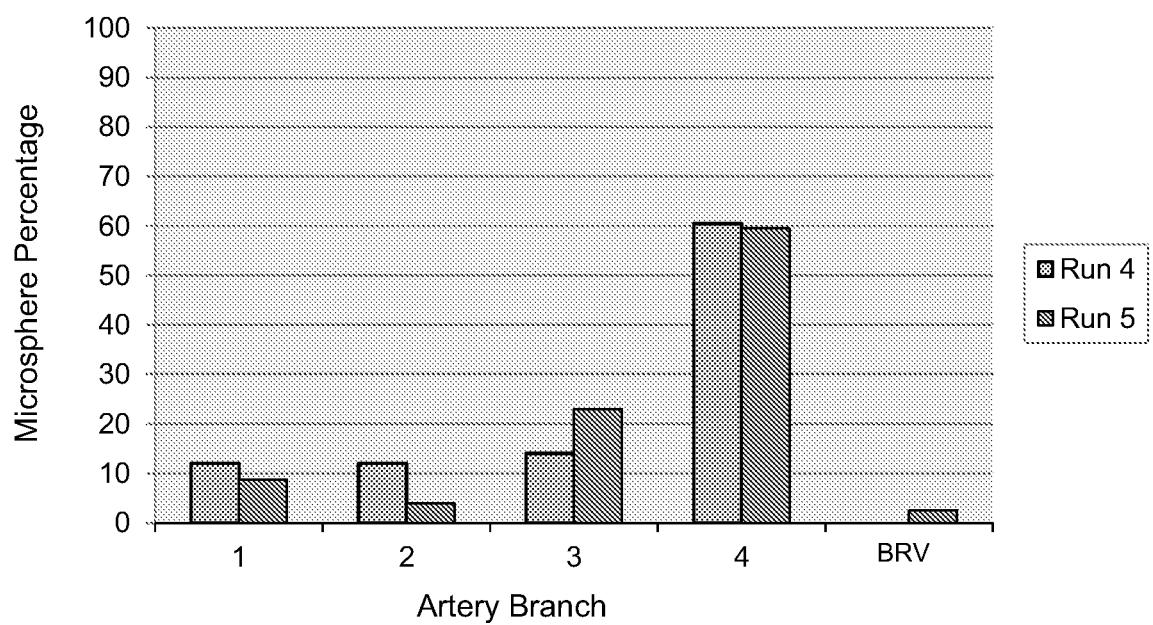

Non-radioactive microspheres (105-150 μm diameter, Polysciences, Inc., Warrington, Pa., United States of America), roughly four times the size of those used in clinical RE procedures, were released from predetermined upstream radial injection locations in the common hepatic artery CHA (see FIG. 20) under steady-flow conditions identical to the CF-PD simulations. Experimental results confirmed the CF-PD predictions, resulting in successful targeting of specific daughter vessels (FIGS. 21a-21c). Repeatability tests confirmed that microsphere distributions vary little between successive runs (FIG. 21d).

Example 8

Refinement of Computational Fluid-Particle Dynamic Models Using Animal-Specific and Patient-Specific Data Medical imaging data (mapping hepatic arterial anatomy) and physiological data sets (blood pressures and velocities upstream/downstream from candidate release sites) are collected from cancer patients and live animal trials. DICOM image data is converted to 3D geometrical models of the hepatic vasculature, while physiological data is collected for realistic inlet/outlet conditions. Simulation results provide patient-specific positioning of the SMC and microsphere and/or drug release profiles.

The medical image (DICOM) files of hepatic tumor patients include geometric characteristics, such as measurement plane with respect to gravitational force direction, bifurcation angles, and length-to-radius ratios. The DICOM files were converted to 3D solid models using appropriate data-file conversion software (e.g., SimpleWare). Injection of angiographic contrast aids in vessel isolation and distinguishing hepatic vasculature from surrounding tissues. Geometries are refined or smoothed as needed to promote convergence while preserving major and minor vessel branches and branch diameters. Physiological flow data sets can include upstream and downstream transient pressure and velocity values. Microsphere and/or drug release conditions and related particle deposition data for representative tumor patients are collected.

Completing pulsatile flow (as opposed to steady-state flow) 3-D simulations typically requires half a week per case, which can be accomplished within the two-week preparation time for treatment. However, an alternative approach, relying on steady-state simulation results, provides coordinates very close to the optimal release location, and reduces computational times to roughly half a day per case. By this method, optimal SMC position can be confirmed/fine-tuned by releasing tagged, biodegradable microspheres from the robotic catheter in situ (during the procedure). High performance computing multi-processor systems can reduce computer-run times to just hours per case.

Example 9

Development of Refined SMC Prototypes for Optimal $^{90}$Y-Microsphere and/or Drug Delivery Catheters were designed and fabricated for precision control of catheter tip position within the hepatic artery (based on the computer simulation results) while minimizing hemodynamic impact. Experiments employed a 4× scale design that could be extended to a 1× prototype. The catheters included a central structural member with tripods positioned at each end and a channel in the center for catheter retention. SMA tendons are connected between the central support and each tripod leg, similar to the placement of biological muscles. Contraction of the tendons creates a moment about the connection pin for each tripod leg. An antagonistic configuration of tendons provides two-way motion of each tripod leg.

Using dynamic pressurization and advanced microsphere and/or drug tracking techniques allows precise microsphere and/or drug delivery. Patient-specific hemodynamic conditions, i.e., pressure and flow fields, are accurately replicated in the hepatic artery model with a pulse duplication system. The optimal SMC outside diameter and orientation is refined via computational fluid-particle dynamics simulations. Designs which minimize fluid disturbance created by the immersed device and minimize forces on the arterial walls while ensuring stable device positioning are used. The inner lumen diameter of the robotic catheter is designed for optimal microsphere and/or drug release. Considerations include avoiding stasis (halting fluid flow) of fluids, as this would clearly hinder transport of microspheres as predicted by computer simulations.

Tendon activation employs heating (Joule heating) of the tendon by transmitting an electrical current through its length. To prevent injury to the patient and ensure proper activation of the tendon, the SMA is adequately insulated from the blood in which the catheter is immersed. SMA actuators are encapsulated in a polymer sheath covering the catheter, with tripod legs penetrating through the sheath. A compliant material, such as silicone rubber, can be utilized as a barrier material to accommodate motion while serving to isolate the tendons from the patient's blood. All device components are biocompatible.

Various methods are used for quantifying microsphere and/or drug concentrations passing through each daughter vessel. In one method, specialized, fluorescent microspheres (Cospheric, Inc., Santa Barbara, Calif., United States of America) are used in combination with light emitting diodes of a specific emission wavelength. These fluorescent spheres absorb light in the near-UV spectrum (365 nm) and emit light in the visible spectrum (561 nm), which is detected using ambient light sensors, such as the TEMT6000 (Vishay Intertechnology, Inc., Malvern, Pa., United States of America). In this method, the vessel walls are transparent, or the spheres pass through a measurement chamber, connected in-line with the daughter vessels. An alternative, using magnetic fields, detects microspheres through the vessel walls; thus, minimizing flow disturbances due to the measurement method. With this technique, a constant magnetic field is applied across each daughter vessel. As paramagnetic microspheres (Cospheric, Inc.) pass through the daughter vessels and through the magnetic field, they become "magnetized" and alter the field. The change in field strength is be detected using giant magnetoresistance (GMR) sensors such as the AAH-002 (NVE Corporation, Eden Prarie, Minn., United States of America). GMR sensors are thin-film based sensors that have extremely high sensitivity to applied magnetic fields. Computer-controlled syringe pumps allow precise dosing of microspheres. The proposed pump can be purchased off-the-shelf or developed within the laboratory.

1× prototypes and hepatic artery models based on injection castings from porcine cadaver anatomy are tested. A silicone or urethane based compound is injected into the hepatic vessels at physiological pressures. The hardened casting is removed either manually or by corrosion casting methods.

With corrosion casting, once the cast has hardened, the biological tissue is macerated in a caustic solution (10% potassium hydroxide) followed by boiling water until residual tissue has been removed. The non-contact nature of this technique may be necessary to preserve the integrity of smaller sized vessels. The extracted cast can then be scanned by a 3D laser scanner, such as the Roland Picza LPX-250 scanner (Roland DGA Corporation, Irvine, Calif., United States of America). Software is then be used to create 3D solid models from scanned 3D points. The resulting geometry is utilized both for CF-PD models and for rapid-prototyping anatomically accurate models. Trajectories of 30 μm microspheres are monitored, compared to CF-PD simulations in steady and dynamic flow experiments. Successful implementation of a microsphere and/or drug detecting method not dependent on transparency of the vessels facilitates live animal studies.

Accurate placement of the catheter tip employs accurate measurement of tip position within the vessel without the benefit of direct visualization. Options for measurement of tip position include electromagnetic (EM) 3D tracking systems (e.g., the 3D Guidance trakSTAR, Ascension Technology Corp., Burlington, Vt., United States of America) and the Ensite NavX 3D navigation system (St. Jude Medical, St. Paul, Minn., United States of America), both of which can measure X-Y-Z coordinates and angular position. Electromagnetic tracking systems are economical and can be easily integrated with a personal computer, but they employ sensing probes located at or near the catheter tip. The Ensite NavX does not employ any dedicated EM sensors within the catheter; however, use of the EnSite NavX system employs an uninterrupted electrical path (through solid or liquid matter) between the patches and electrodes.

The computational work necessary for obtaining optimal microsphere and/or drug release position (i.e., catheter tip location) and optimal microsphere and/or drug selection employs patient-specific data.

Example 10

Surgical Validation of Selective Targeting Using these Computational Models and SMC Prototypes Non-radioactive microspheres are delivered into porcine hepatic vasculature using SMC prototypes at locations prescribed by computer simulation results. Following microsphere and/or drug deployment, the distribution of microspheres in the hepatic arterial branches is evaluated (using medical imaging and dissection) to quantify and validate the effectiveness of selective targeting.

Prior to each procedure, each animal undergoes non-invasive DICOM imaging to map hepatic arterial geometries, including measurement plane with respect to gravitational force, bifurcation angles, and length-to-radius ratios. Magnetic resonance imaging (MRI) scanning capabilities are utilized for this purpose. Non-invasive techniques are used to measure physiological flow data upstream and downstream from potential particle release sites. After image conversion and flow-data analysis, vessel geometry and pressure profiles are uploaded to CF-PD software to provide animal-specific flow simulations and predict particle destinations relative to particle release position (axial and radial) of the new catheter design. Since the diameters of hepatic arterial supplies can limit the axial positioning of the catheter, potential particle release points are filtered to those locations to which the catheter can navigate.

After non-invasive data collection and completion of computational fluid-particle dynamics simulations, each animal undergoes surgical procedures replicating radioembolization in the treatment of hepatic cancers. These trials are completed in situ or in vivo or a combination of both. With in situ tests, the animal is euthanized prior to the treatment procedure. The aorta or vessel branching from the aorta to the hepatic arterial supply is cannulated to provide a regulated flow of perfusate to the hepatic arterial branches. The vena cava will be incised (or cannulated) to allow for blood flow through the liver and the venous vessels. With in situ testing, pressure waveforms are controlled and can be input as boundary conditions to the CF-PD simulations. With in vivo testing, the animal is anesthetized prior to surgical evaluations; arterial blood supply is provided by the beating heart. At an intermediate stage, the abdominal cavity can be opened for direct insertion of the catheter into the hepatic artery under line-of-sight visualization. At advanced stages of testing, fluoroscopy is employed, as needed, throughout each procedure for catheter insertion via the femoral artery, as this is the primary access method for RE.

After introduction into the hepatic vasculature, catheter displacement is monitored in real-time via direct visualization, 3D tracking technologies, or fluoroscopy, according to the test condition. A target "tumor" site is assigned to each animal. The operator positions the catheter tip at the optimal release zone as prescribed by the animal-specific CF-PD simulations. After verifying the radial and axial position of the nozzle, microspheres are released into the arterial supply in distributions comparable to that of radioembolization procedures. Technetium (Tc)-99m microspheres are used for this experiment since they emit easily detectable gamma rays and have a short half life (~6 hours). Arterial fluid supply (blood or solution) is maintained long enough to establish the microspheres within their target locations. With in vivo testing, the animal is euthanized at this time. Following microsphere and/or drug deployment, the animal is tested to quantify the distribution of microspheres in the major hepatic arterial branches. SPECT is one option for detecting radioactive microspheres within the hepatic animal tissues. SPECT detects gamma-emitting isotopes in a slice-by-slice manner, similar to MRI or CT, and stores results in DICOM data format. Nuclear medicine imaging is another option.

Alternative robotic catheters employ, as an alternative to 3D sensing technologies in animal testing, the radial SMC-position calculated by sensing resistances in the SMA tendons, since material (SMA) strain is related to changes in electrical resistance. These strain values are used to calculate the deployment of each tripod and thus the radial position of the catheter nozzle.

Example 11

Imaging Validation in Clinical Trials

Clinical trials involving 15 human patients with unresectable hepatic cancers (primary and metastatic) are conducted to validate the technology and procedural methodology. A doctor obtains enhanced images of a patient's hepatic artery system and tumor. Pressure and flow rate data are also collected. Medical data analysis can include image file conversion for flow domain meshing and computer-model parameter inputs and model validation. Computer simulations provide results for both optimal SMC-position and $^{90}$Y-microsphere and/or drug release and allow complementary biodegradable particle release for confirmation/fine-tuning of optimal, patient-specific SMC positioning. Treatment is implemented with SMC-Syringe-Microprocessor setting for telemetric operations and includes optimal $^{90}$Y-microsphere and/or drug release and targeting of tumors.

Patients are treated with $^{90}$Y-microspheres released into the hepatic artery to permanently implant into hepatic tumors. During pre-treatment planning, Computed Tomography Angiography (CTA) via the SMC system allows 3D reconstruction of the images providing confirmation of targeting of the tumors. Subsequently, at treatment (usually 7 days later) the position of the test catheter is reproduced from the pre-treatment planning session, and CTA is repeated prior to delivery of $^{90}$Y microspheres for anti-cancer therapy.

Follow-up axial imaging (usually CT) of the liver is performed at 6 and 12 weeks after radiation delivery. Comparison of planning and treatment imaging to follow-up imaging shows response to treatment. Clinical data (tumor markers, liver function tests) from blood and physical exams is used to corroborate outcomes suggested by the imaging. $Y^{90}$ microsphere and/or drug deposition efficiencies, including local particle clustering (i.e., "hot spots"), from already available data employing a standard catheter is compared to data obtained with the novel robotic catheter. Follow up extends up to 12 weeks post-treatment for outcome analysis.

REFERENCES

The references listed below, as well as all references cited in the specification, are incorporated herein by reference to the extent that they supplement, explain, provide a background for, or teach methodology, techniques, and/or compositions employed herein.

1. Breedis C, Young G. The blood supply of neoplasms in the liver. *Am J Pathol* 1954; 30:969-984.
2. Kennedy A, Nag S, Salem R, et al. Recommendations for radioembolization of hepatic malignancies using yttrium-90 microsphere brachytherapy: a consensus panel report from the radioembolization brachytherapy oncology consortium. *Int J Radiat Oncol Biol Phys* 2007; 68:13-23.

3. Kennedy A S, Nutting C, Coldwell D, et al. Pathologic response and microdosimetry of 90Y microspheres in man: Review of four explanted whole livers. *Int J Radiat Oncol Biol Phys* 2004; 60:1552-1563.
4. Salem R, Thurston K G. Radioembolization with 90Yttrium Microspheres: A State-of-the-Art Brachytherapy Treatment for Primary and Secondary Liver Malignancies: Part 1: Technical and Methodologic Considerations. *J Vasc Interv Radiol* 2006; 17:1251-1278.
5. Salem R, Thurston K G. Radioembolization with yttrium-90 microspheres: a state-of-the-art brachytherapy treatment for primary and secondary liver malignancies: part 3: comprehensive literature review and future direction. *J Vasc Interv Radiol* 2006; 17:1571-1593.
6. Salem R, Thurston K G. Radioembolization with 90yttrium microspheres: a state-of-the-art brachytherapy treatment for primary and secondary liver malignancies. Part 2: special topics. *J Vasc Interv Radiol* 2006; 17:1425-1439.
7 Sato K T, Lewandowski R J, Mulcahy M F, et al. Unresectable chemorefractory liver metastases: radioembolization with 90Y microspheres—safety, efficacy, and survival. *Radiology* 2008; 247:507-515.
8. Kleinstreuer C. Analyses of Arterial Diseases. In: Biofluid Dynamics: Principles and Selected Applications. Boca Raton: Taylor & Francis; 2006. pp. 247-276.
9. Kleinstreuer C. Case Studies in Biofluid Dynamics. In: Biofluid Dynamics: Principles and Selected Applications. Boca Raton: Taylor & Francis; 2006. pp. 397-419.
10. Hashimoto K, et al. Quantitative tissue blood flow measurement of the liver parenchyma: comparison between xenon CT and perfusion CT. *Dig Dis Sci* 2007; 52:943-949.
11. Hubner G H, et al. Hepatic arterial blood flow velocities: assessment by transcutaneous and intravascular Doppler sonography. *J Hepatol* 2000; 32:893-899.
12. Ishigami K, et al. Does variant hepatic artery anatomy in a liver transplant recipient increase the risk of hepatic artery complications after transplantation? *AJR Am J Roentgenol* 2004; 183:1577-1584.
13. Radeleff B, Sommer C M, Heye T, et al. Acute increase in hepatic arterial flow during TIPS identified by intravascular flow measurements. *Cardiovasc Intervent Radiol* 2009; 32:32-37.
14. Buchanan J R, Kleinstreuer C, Corner J K. Rheological effects on pulsatile hemodynamics in a stenosed tube. *Computers & Fluids* 2000; 29:695.
15. Kleinstreuer C. Biofluid Mechanics of Organ Systems. In: Biofluid Dynamics: Principles and Selected Applications. Boca Raton: Taylor & Francis; 2006. pp. 339-351.
16. Kleinstreuer C, et al. A new methodology for targeting drug-microspheres in the human respiratory system. *International Journal of Heat & Mass Transfer* 2008; 51:5578-5589.
17. Kleinstreuer C, Zhang Z. An adjustable triple-bifurcation unit model for air-particle flow simulations in human tracheobronchial airways. *Journal of Biomechanical Engineering (ASME)* 2009; 131:21007.
18. Zhang Z, Kleinstreuer C, Kim C. Gas-solid two-phase flow in a triple bifurcation lung airway model. *International Journal of Multiphase Flow* 2002; 28:1021-1046.
19. Zhang Z, Kleinstreuer C, Kim C. Micro-particle transport and deposition in a human oral airway model. *Journal of Microsphere Science* 2002; 33:1635-1652.
20. Bushi D, Grad Y, Einav S, et al. Hemodynamic evaluation of embolic trajectory in an arterial bifurcation: an in-vitro experimental model. *Stroke* 2005; 36:2696-2700.
21. Atassi B, Bangash A K, Bahrani A, et al. Multimodality imaging following 90Y radioembolization: a comprehensive review and pictorial essay. *Radiographics* 2008; 28:81-99.
22. Campbell A M, Bailey I H, Burton M A. Analysis of the distribution of intra-arterial microspheres in human liver following hepatic yttrium-90 microsphere therapy. *Phys Med Biol* 2000; 45:1023-1033.
23. Campbell A M, Bailey I H, Burton M A. Tumor dosimetry in human liver following hepatic yttrium-90 microsphere therapy. *Phys Med Biol* 2001; 46:487-498.
24. Kulik L M, Atassi B, van Holsbeeck L, et al. Yttrium-90 microspheres (TheraSphere) treatment of unresectable hepatocellular carcinoma: downstaging to resection, RFA and bridge to transplantation. *J Surg Oncol* 2006; 94:572-586.
25. Ariel I M. Radioactive isotopes for adjuvant cancer therapy. *Archives of Surgery* 1964; 89:244-249.
26. Ariel I M. Treatment of inoperable primary pancreatic and liver cancer by the intra-arterial administration of radioactive isotopes (Y90 radiating microspheres). *Ann Surg* 1965; 162:267-278.
27. Muller J H, Rossier P H. A new method for the treatment of cancer of the lungs by means of artificial radioactivity (Zn63 and Au198). *Acta Radiol* 1951; 35:449-468.
28. Murthy R, Nunez R, Szklaruk J, et al. Yttrium-90 microsphere therapy for hepatic malignancy: devices, indications, technical considerations, and potential complications. *Radiographics* 2005; 25 Suppl 1:S41-55.
29. Mabotuwana T D, Cheng L K, Pullan A J. A model of blood flow in the mesenteric arterial system. *Biomed Eng Online* 2007; 6:17.
30. Ibrahim, S. M., et al., Radiologic findings following Y90 radioembolization for primary liver malignancies. *Abdominal Imaging,* 34:566-581, 2009.
31. Kleinstreuer, C; Zhang, Z. and Donohue, J. F. Targeted drug-aerosol delivery in the human respiratory system. *Annual Review of Biomedical Engineering,* 10:195-220, 2008.
32. Overton, C., et al., Radioembolization for unresectable neuroendocrine hepatic metastases using resin 90Y-microspheres: early results in 148 patients. *American Journal of Clinical Oncology,* 31(3): 271-279, 2008.
33. Parkin, D. M., et al., Global Cancer Statistics, 2002. *CA: A Cancer Journal for Clinicians,* 55:74-108, 2005.
34. Salem, R. and Thurston, K. G. Radioembolization with 90Yttrium microspheres: A state-of-the-art brachytherapy treatment for primary and secondary liver malignancies: Part 2: Special Topics. *Journal of Vascular and Interventional Radiology,* 17(9):1425-1439, 2006.
35. Saatchi, K. and Haefeli, U. O. Radiolabeling of biodegradable polymeric microspheres with evaluation using microSPECT/CT imaging. Bioconjugate Chem. 20: 1209-17; 2009
36. Veeramani, A. S., et al. Design and control of a shape memory alloy actuated robotic catheter", *Proceedings of the ASME Dynamic Systems and Control Conference* (DSCC 2008), Oct. 20-22, 2008, Ann Arbor, Mich., USA.
37. Veeramani, A. S., et al., Development of a shape memory alloy actuated catheter for cardiovascular procedures", *Proceedings of the 3rd Annual Frontiers in Biomedical Devices Conference*, Irvine, Calif., June 2008.
38. Veeramani, A. S., et al., Modeling the dynamic behavior of a shape memory alloy actuated catheter. *Smart Materials and Structures,* 17(1):1-4, 2008.
39. Welsh, J. S., et al., Selective internal radiation therapy (SIRT) for liver metastases secondary to colorectal adenocarcinoma. *International Journal of Radiation Oncology•Biology•Physics,* 66(2):S62-S73, 2006.

It will be understood that various details of the presently disclosed subject matter may be changed without departing from the scope of the present subject matter. Furthermore, the foregoing description is for the purpose of illustration only, and not for the purpose of limitation.

What is claimed is:

1. A method of delivering an active agent to a target area of a body of a subject in need thereof, comprising:
   providing a smart micro-catheter (SMC) system for directing into a blood vessel of the subject a controlled stream comprising an active agent, wherein the SMC system comprises a SMC device with an adaptive nozzle inserted in the blood vessel; and
   regulating a release position of the controlled stream from the SMC system to release the active agent in a predetermined manner such that they are delivered to the target area of the body of the subject,
   wherein the SMC system comprises:
   (a) a source of active agent;
   (b) an injection system in flow communication with the source of active agent; and
   (c) a SMC device in flow communication with the injection system, comprising:
      (i) a tube having an inlet at one end, an outlet at an opposing end, and a wall joining the inlet and the outlet;
      (ii) an adaptive nozzle positioned within the blood vessel and having a nozzle inlet engaged with the tube outlet and a nozzle tip outlet distal to the tube outlet, wherein the nozzle tip outlet and the nozzle inlet are in flow communication and adapted for passage of a stream comprising an active agent therebetween; and
      (iii) one or more actuators operationally linked to the adaptive nozzle, wherein the one or more actuators can position the nozzle tip outlet and thereby regulate the stream release from the SMC device,
   wherein the catheter is manually operated to achieve the desired axial position and electro-mechanically operated to achieve the desired radial position, and wherein the catheter further comprises two stent rings with adjustable tripod struts and SMA-wires, folded in the nozzle area, which are deployed by electric current to position the nozzle plus nozzle tip according to the predetermined coordinates via a feedback control loop based on position sensor signals and a subject-specific microprocessor program.

2. A method of delivering an active agent to a target area of a body of a subject in need thereof, comprising:
   providing a smart micro-catheter (SMC) system for directing into a blood vessel of the subject a controlled stream comprising an active agent, wherein the SMC system comprises a SMC device with an adaptive nozzle inserted in the blood vessel; and
   regulating a release position of the controlled stream from the SMC system to release the active agent in a predetermined manner such that they are delivered to the target area of the body of the subject,
   wherein the SMC system comprises:
   (a) a source of active agent;
   (b) an injection system in flow communication with the source of active agent; and
   (c) a SMC device in flow communication with the injection system, comprising:
      (i) a tube having an inlet at one end, an outlet at an opposing end, and a wall joining the inlet and the outlet;
      (ii) an adaptive nozzle positioned within the blood vessel and having a nozzle inlet engaged with the tube outlet and a nozzle tip outlet distal to the tube outlet, wherein the nozzle tip outlet and the nozzle inlet are in flow communication and adapted for passage of a stream comprising an active agent therebetween; and
      (iii) one or more actuators operationally linked to the adaptive nozzle,
   wherein the one or more actuators can position the nozzle tip outlet and thereby regulate the stream release from the SMC device,
   wherein the one or more actuators comprise an active material, and
   wherein the SMC device further comprises a stent ring with adjustable tripod legs and SMA-wires, folded in the nozzle area, which are deployed by electric current to position the nozzle and nozzle tip and wherein the one or more actuators include two actuators antagonistic to each other allowing two way motion of the tripod leg.

\* \* \* \* \*